United States Patent
Sawada et al.

(10) Patent No.: US 10,504,732 B2
(45) Date of Patent: Dec. 10, 2019

(54) IMPURITY DIFFUSION AGENT COMPOSITION AND METHOD FOR MANUFACTURING SEMICONDUCTOR SUBSTRATE

(71) Applicant: TOKYO OHKA KOGYO CO., LTD., Kawasaki-shi (JP)

(72) Inventors: Yoshihiro Sawada, Kawasaki (JP); Yu Takahashi, Kawasaki (JP)

(73) Assignee: TOKYO OHKA KOGYO CO, LTD., Kawasaki-Shi (JP)

( * ) Notice: Subject to any disclaimer, the term of this patent is extended or adjusted under 35 U.S.C. 154(b) by 101 days.

(21) Appl. No.: 15/845,015

(22) Filed: Dec. 18, 2017

(65) Prior Publication Data

US 2018/0182624 A1 Jun. 28, 2018

(30) Foreign Application Priority Data

Dec. 22, 2016 (JP) .................................. 2016-249961
Nov. 28, 2017 (JP) .................................. 2017-228267

(51) Int. Cl.
| | | |
|---|---|---|
| H01L 21/22 | (2006.01) | |
| H01L 21/02 | (2006.01) | |
| C07F 5/02 | (2006.01) | |
| C07F 5/00 | (2006.01) | |

(52) U.S. Cl.
CPC ............ *H01L 21/2225* (2013.01); *C07F 5/00* (2013.01); *C07F 5/022* (2013.01); *H01L 21/02052* (2013.01)

(58) Field of Classification Search
None
See application file for complete search history.

(56) References Cited

U.S. PATENT DOCUMENTS

2016/0099149 A1* 4/2016 Sawada ............... H01L 21/2225
438/558

FOREIGN PATENT DOCUMENTS

| JP | H06-318559 A | 11/1994 |
|---|---|---|
| WO | WO 2014/064873 A1 | 5/2014 |

* cited by examiner

*Primary Examiner* — Bradley Smith
(74) *Attorney, Agent, or Firm* — Knobbe, Martens, Olson & Bear LLP

(57) ABSTRACT

A diffusion agent composition that can be evenly applied onto the whole area of an inner surface of the fine voids, whereby boron can be well and uniformly diffused into the semiconductor substrate even by heating at a low temperature, and a method for manufacturing a semiconductor substrate using the diffusion agent composition. In a diffusion agent composition including an impurity diffusion component, the impurity diffusion component, which can be applied onto a surface of a semiconductor substrate to form a diffusion layer, and which is a boron compound including a nitrogen atom, is used.

8 Claims, No Drawings

IMPURITY DIFFUSION AGENT COMPOSITION AND METHOD FOR MANUFACTURING SEMICONDUCTOR SUBSTRATE

This application claims priority to Japanese Patent Application No. 2016-249961, filed Dec. 22, 2016, and Japanese Patent Application No. 2017-228267, filed Nov. 28, 2017, the entire contents of which are incorporated herein by reference.

BACKGROUND OF THE INVENTION

Field of the Invention

The present invention relates to a diffusion agent composition as an impurity diffusion component which can be applied onto a surface of a semiconductor substrate to form a diffusion layer and which contains a boron compound including a nitrogen atom, and a method for manufacturing a semiconductor substrate in which an impurity diffusion component is diffused into a semiconductor substrate by a thin film formed using the diffusion agent composition.

Related Art

Semiconductor substrates used in semiconductor elements such as transistors, diodes and solar batteries are manufactured by diffusing impurity diffusion components such as phosphorus and boron into the semiconductor substrates. For such semiconductor substrates, in the manufacture of semiconductor substrates for multigate elements such as Fin-FET and nanowire FET, in some cases, for example, impurities are diffused into semiconductor substrates having on their surface a three-dimensional structure having nanometer-scale fine voids.

For example, an ion implantation method (see, for example, Patent Document 1) and a CVD method (see, for example, Patent Document 2) are known as methods for diffusion of an impurity diffusion component into the semiconductor substrate. In the ion implantation method, an ionized impurity diffusion component is implanted into a surface of a semiconductor substrate. In the CVD method, an impurity diffusion component is diffused from an oxide film into a semiconductor substrate by forming, on the semiconductor substrate, an oxide film of silicon oxide or the like doped with impurity diffusion components such as phosphorus and boron by CVD, and then heating the semiconductor substrate provided with the oxide film formed thereon in an electric furnace or the like.

Patent Document 1: Japanese Unexamined Patent Application, Publication No. H06-318559
Patent Document 2: PCT International Publication No. WO2014/064873

SUMMARY OF THE INVENTION

In an ion implantation method disclosed in Patent Document 1, however, when light ions like B (boron) are implanted into a semiconductor substrate, point defects and point defect clusters are likely to be formed in areas near the surface of the substrate. For example, when CMOS elements such as CMOS image sensors are formed by diffusing an impurity diffusion component into a semiconductor substrate by the ion implantation method, the occurrence of such defects is directly linked to deterioration of performance of elements.

Further, when the semiconductor substrate has on its surface a three-dimensional structure such as a nanoscale three-dimensional structure for the formation of a multigate element called Fin-FET including a plurality of source fins, a plurality of drain fins, and a gate vertical to these fins, in the ion implantation method, it is difficult to uniformly implant ions into a side surface and an upper surface of the fins and the gate, and the whole area of an inner surface of concave portion surrounded by the fins and the gate.

In the diffusion of the impurity diffusion component by the ion implantation method into the semiconductor substrate having a nanoscale three-dimensional structure, even when ions could have been uniformly implanted, the following problem occurs. For example, when logic LSI devices and the like are formed using a semiconductor substrate having a three-dimensional pattern including fine fins, crystals of substrate materials such as silicon are likely to be broken by ion implantation. Such damage to the crystals is considered to cause problems of a variation in properties of the device and the occurrence of stand-by leak current.

Further, the CVD method as described in Patent Document 2 is employed, a problem of, due to an overhang phenomenon, being difficult to cover the whole inner surface of concave portions surrounded by the fins and the gate with an oxide film that is uniform in thickness and contains an impurity diffusion component, as well as a problem of an oxide being deposited in openings of recess portions surrounded by the fins and the gate thereby blocking the openings. Thus, in the ion implantation method and the CVD method, an impurity diffusion component cannot be diffused well and uniformly on semiconductor substrates without difficulties, depending upon surface shapes of the semiconductor substrate.

In order to solve such problems, a coat-type diffusion agent composition is considered to be used. On a substrate having a three-dimensional structure having nanoscale fine voids on the surface thereof, when the coat-type diffusion agent compositions can be uniformly applied onto the whole surface including the whole area of an inner surface of the fine voids, impurities such as boron can be diffused uniformly in a semiconductor substrate having such a three-dimensional surface. Furthermore, the coat-type diffusion agent composition is demanded to satisfactorily diffuse impurities even when a cycle of temperature-raising and cooling is becoming shorter, or when heating is carried out at a low temperature. With trend to three-dimensional structure, controlling of diffusion length is further necessary. However, it can be considered that when diffusion is carried out by heating at a low temperature, the length of diffusion can be shortened.

The present invention has been made in view of the above problems, and an object of the present invention is to provide a diffusion agent composition that can be evenly applied onto the whole area of an inner surface of the fine voids, even when a semiconductor substrate as an object into which an impurity diffusion component is to be diffused has, on a surface thereof, a surface provided with a three-dimensional structure having nanoscale fine voids, whereby boron can be well and uniformly diffused into the semiconductor substrate even by heating at a low temperature such as not higher than 1000° C., and also provide a method for manufacturing a semiconductor substrate using the diffusion agent composition.

The present inventors have found that the above problems can be solved by using an impurity diffusion component (A) which can be applied onto a surface of a semiconductor substrate to form a diffusion layer and which is a boron compound including a nitrogen atom, in a diffusion agent composition including an impurity diffusion component (A), and has completed the present invention. More specifically, the present invention provides the following matters.

A first aspect of the present invention is a diffusion agent composition used for diffusion of impurities into a semiconductor substrate,
including an impurity diffusion component (A), wherein the impurity diffusion component (A) is a diffusion component which can be applied onto a surface of a semiconductor substrate to form a diffusion layer, and which is a boron compound including a nitrogen atom.

A second aspect of the present invention is a method for manufacturing a semiconductor substrate, the method including: applying the diffusion agent composition according to the first aspect onto the semiconductor substrate to form a coating film; and
diffusing the impurity diffusion component (A) in the diffusion agent composition into the semiconductor substrate.

The present invention can provide a diffusion agent composition that can be evenly applied onto the whole area of an inner surface of the fine voids, even when a semiconductor substrate as an object into which an impurity diffusion component is to be diffused has, on a surface thereof, a surface provided with a three-dimensional structure having nanoscale fine voids, whereby boron can be well and uniformly diffused into the semiconductor substrate even by heating at a low temperature such as not higher than 1000° C., and also provide a method for manufacturing a semiconductor substrate using the diffusion agent composition.

DETAILED DESCRIPTION OF THE INVENTION

<<Diffusion Agent Composition>>

A diffusion agent composition is to be used for diffusion of impurities into a semiconductor substrate, and includes an impurity diffusion component (A). The impurity diffusion component (A) can be applied onto a surface of a semiconductor substrate to form a diffusion layer, and is a boron compound including a nitrogen atom. The use of such an impurity diffusion component (A) allows boron to be well diffused into the semiconductor substrate with the diffusion agent composition. Furthermore, even when a semiconductor substrate as is an object into which an impurity diffusion component is to be diffused has a three-dimensional structure having nanoscale fine voids on a surface thereof, the use of the above-mentioned diffusion agent composition can allow the diffusion agent composition to be evenly applied onto a surface of the semiconductor substrate including the whole area of the inner surface of the fine voids. Thus, boron is uniformly diffused into the semiconductor substrate.

Indispensable or optional components contained in the diffusion agent composition will be described.

[Impurity Diffusion Component (A)]

The impurity diffusion component (A) can be applied onto a surface of a semiconductor substrate to form a diffusion layer, and is a boron compound including a nitrogen atom. For example, it is considered that a boron compound including a nitrogen atom is arranged on the substrate surface to a thickness of one to several molecules level so as to form a diffusion layer by adsorption onto the substrate surface by an unshared electron pair possessed by a nitrogen atom, or adsorption onto the substrate surface when a boron compound has organic groups such as an alkyl group (in particular, a hydrocarbon group). Furthermore, from the viewpoint of adsorptivity of a boron compound onto the substrate surface, it is preferable that a boron atom in a boron compound is not in a tetravalent state. Examples of a boron compound in which a boron atom is in a tetravalent state include a complex compound such as a complex of triethylamine and $BH_3$.

Examples of the boron compound satisfying the above-mentioned predetermined conditions preferably include a compound represented by, for examples, the following formula (a1) or formula (a2):

(in the formula (a1), $R^1$, $R^2$, $R^3$, and $R^4$ each independently represent a hydrogen atom, a hydroxyl group, an organic group which does not contain a nitrogen atom, or a nitrogen atom-containing group; at least one of $R^1$, $R^2$, $R^3$, and $R^4$ is a nitrogen atom-containing group; and $R^1$ and $R^2$, $R^2$ and $R^4$, $R^3$ and $R^4$, as well as $R^1$ and $R^3$, each independently, may be bonded to each other to form a ring;
in the formula (a2), $R^5$, $R^6$, and $R^7$ each independently represent a hydrogen atom, a hydroxyl group, an organic group which does not contain a nitrogen atom, or a nitrogen atom-containing group; at least one of $R^5$, $R^6$, and $R^7$ is a nitrogen atom-containing group; and two of $R^5$, $R^6$, and $R^7$ may be bonded to each other to form a ring).

In the formula (a1), the organic group which does not contain a nitrogen atom as $R^1$, $R^2$, $R^3$, and $R^4$ may include a heteroatom other than a nitrogen atom. Examples of the heteroatom include O, S, B, and the like.

The organic group which does not contain a nitrogen atom as $R^1$, $R^2$, $R^3$, and $R^4$ is not particularly limited, but preferable examples include a group represented by —$R^{a1}$, and a group represented by —O—$R^{a1}$. $R^{a1}$ is a hydrocarbon group which may have a substituent, or a heterocyclyl group which may have a substituent.

When $R^{a1}$ is a hydrocarbon group which may have a substituent, examples of suitable hydrocarbon group include alkyl, aliphatic cyclic, cycloalkyl alkyl, alkenyl, and aromatic hydrocarbon groups. The number of carbons of the hydrocarbon group is not particularly limited, but it is preferably 1 to 20, more preferably 1 to 10, and particularly preferably 1 to 6.

The alkyl group may be a straight-chain group or a branched-chain group. Examples of suitable alkyl groups include methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-icosyl groups.

The aliphatic cyclic group may be a monocyclic group or a polycyclic group. Examples of the monocyclic group include cycloalkyl groups such as a cyclopentyl group, a cyclohexyl group, and a cycloheptyl group. Examples of the polycyclic group include adamanthyl, norbornyl, isobornyl, tricyclononyl, tricyclodecyl, and tetracyclodecyl groups, and the like.

Examples of the cycloalkyl alkyl group include cyclopentyl methyl, 2-cyclopentyl ethyl, 3-cyclopentyl propyl, 4-cyclopentyl butyl, cyclohexyl methyl, 2-cyclohexyl ethyl, 3-cyclohexyl propyl, and 4-cyclohexyl butyl groups.

The alkenyl group may be a straight-chain group or a branched-chain. Examples of suitable alkenyl groups include alkenyl groups corresponding to the above-mentioned examples of the suitable alkyl groups. Examples of the particularly preferable alkenyl groups include a vinyl group and an allyl group.

Examples of suitable aromatic hydrocarbon group include phenyl, naphthyl, and biphenylyl groups. Among them, a phenyl group is preferable.

When $R^{a1}$ is a heterocyclyl group which may have a substituent, the heterocyclyl group is not particularly limited as long as it is a heterocyclyl group which does not contain a nitrogen atom. Examples of suitable heterocyclyl group include furanyl, thienyl, pyranyl, thiopyranyl, tetrahydro furanyl, and tetrahydrothienyl groups.

When $R^{a1}$ is a group having a substituent, examples of suitable substituent include an alkyl group having 1 to 6 carbon atoms, an alkoxy group having 1 to 6 carbon atom, a hydroxyl group, a mercapto group, an aliphatic acyloxy group having 2 to 7 carbon atoms, a benzoyl group, an alkoxycarbonyl group having 2 to 7 carbon atoms, a phenoxycarbonyl group, and the like. When $R^{a1}$ has a plurality of substituents, the plurality of substituents may be different from each other.

When $R^1$, $R^2$, $R^3$, and $R^4$ are nitrogen atom-containing groups, the nitrogen atom-containing groups may be an organic group or an inorganic group. Examples of suitable nitrogen atom-containing groups include an amino group, an isocyanate group, and organic groups including a nitrogen atom.

Examples of the organic groups including a nitrogen atom include a group represented by —$NHR^{a1}$, a group represented by —$N(R^{a1})_2$, a group represented by —$R^{a2}$—$(R^{a3})_p$, and a group represented by —O—$R^{a2}$—$(R^{a3})_p$, and the like. $R^{a1}$ is as mentioned above. When the organic group including a nitrogen atom include a plurality of $R^{a1}$s, the plurality of $R^{a1}$s in the organic group may be different from each other. Examples of suitable $R^{a2}$ are the same as those described for $R^{a1}$. $R^{a2}$ is a group having a valence of (p+1) in which p hydrogen atoms are removed from the above-mentioned $R^{a1}$. $R^{a3}$ is a group selected from the group consisting of a nitro group, a cyano group, an amino group, an isocyanate group, a mono- or dialkyl amino group having 1 to 6 carbon atoms, and a carbamoyl group. When the organic group including a nitrogen atom includes a plurality of $R^{a3}$s, the plurality of $R^{a3}$s in the organic group may be different from each other. P is a number of substitution of —$R^{a3}$ in the group represented by —O—$R^{a2}$—$(R^{a3})_p$. P is an integer of one or more. The upper limit of p can be appropriately determined depending on the number of carbon atoms in $R^{a2}$. P is typically an integer of preferably 1 to 6, more preferably 1 to 3, particularly preferably 1 or 2, and most preferably 1.

In the formula (a1), $R^1$ and $R^2$, $R^2$ and $R^4$, $R^3$ and $R^4$, as well as $R^1$ and $R^3$, each independently, may be bonded to each other to form a ring. In this case, a divalent group formed in which $R^1$ and $R^2$, $R^2$ and $R^4$, $R^3$ and $R^4$, as well as $R^1$ and $R^3$ are each bonded to each other include groups represented by the following formulae (i) to (viii).

—$NR^{a4}$—$R^{a5}$—$NR^{a4}$— (i)

 (ii)

—$NR^{a4}$—BH—BH—$NR^{a4}$— (iii)

—$NR^{a4}$—BH—$NR^{a4}$—$NR^{a4}$— (iv)

—$NR^{a4}$—$NR^{a4}$—$NR^{a4}$—$NR^{a4}$— (v)

—$NR^{a4}$—BH—$NR^{a4}$—BH—$NR^{a4}$— (vi)

—O—$R^{a5}$—O— (vii)

—O—$R^{a6}$—O— (viii)

In the above-mentioned formulae (i) to (viii), $R^{a4}$ is a hydrogen atom, a group represented by —$R^{a1}$, a group represented by —O—$R^{a1}$, or a group represented by —CO—$R^{a1}$—. $R^{a4}$ in the above-mentioned formulae (i) to (viii) may be the same as or different from each other. $R^{a5}$ in the formula (i) and the formula (vii) may be a straight-chain alkylene group or a branched-chain alkylene group. Examples of suitable alkylene groups include —$CH_2CH_2$—, —$CH_2CH_2CH_2$—, —$CH_2CH_2CH(CH_2CH_3)$—, —$CH_2CH_2CH(CH_2CH_3)$—, —$CH_2$—$C(CH_3)_2$—$CH_2$—, and —$C(CH_3)_2C(CH_3)_2$—. $R^{a6}$ in the formula (viii) is a divalent group in which two hydroxyl groups are removed from a tartaric acid amide compound.

$R^5$, $R^6$, and $R^7$ in the formula (a2) each independently represent a hydrogen atom, a hydroxyl group, an organic group which does not contain a nitrogen atom, or a nitrogen atom-containing group. Examples of these groups are the same as those described for $R^1$, $R^2$, $R^3$, and $R^4$ in the formula (a1).

Furthermore, in the formula (a2), two of $R^5$, $R^6$, and $R^7$ may be bonded to each other to form a ring. In this case, examples of a divalent group formed by bonding $R^5$ and $R^6$, $R^6$ and $R^7$, or $R^5$ and $R^7$ include groups represented by the above-mentioned formulae (i) to (vi).

Hereinafter, examples of suitable compounds represented by the formula (a1) and examples of suitable compounds represented by the formula (a2) are described in detail.

Examples of suitable compounds represented by the formula (a1) include a compound represented by the following formula (a1-1):

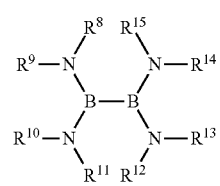 (a1-1)

(in the formula (a1-1), $R^8$ to $R^{15}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms; $R^8$ and $R^9$, $R^{10}$ and $R^{11}$, and $R^{12}$ and $R^{13}$, as well as $R^{14}$ and $R^{15}$, each independently, may be bonded to each other to form a ring).

Aliphatic hydrocarbon groups as $R^8$ to $R^{15}$ may be a straight-chain group or a branched-chain group, and may be a saturated hydrocarbon group or an unsaturated hydrocarbon group. The aliphatic hydrocarbon groups as $R^8$ to $R^{15}$ are preferably straight-chain saturated hydrocarbon group. The number of carbon atoms in the aliphatic hydrocarbon groups as $R^8$ to $R^{15}$ is preferably 1 to 6, more preferably 1 to 4, and particularly preferably 1 to 3. Examples of suitable aliphatic hydrocarbon groups as $R^8$ to $R^{15}$ include methyl, ethyl, n-propyl, isopropyl, n-butyl, isobutyl, sec-butyl, tert-butyl, n-heptyl, n-hexyl, n-heptyl, n-octyl, 2-ethyl hexyl, n-nonyl, and n-decyl groups. Methyl, ethyl, n-propyl, and isopropyl groups are preferable. Methyl and ethyl groups are more preferable.

The number of carbon atoms in the aromatic hydrocarbon group as $R^8$ to $R^{15}$ is preferably 6 to 10. Examples of suitable aromatic hydrocarbon groups as $R^8$ to $R^{15}$ include phenyl, α-naphthyl, and β-naphthyl groups. A phenyl group is preferable.

The number of carbon atoms in the aralkyl group as $R^8$ to $R^{15}$ is 7 to 12. Examples of suitable aralkyl group as $R^8$ to $R^{15}$ include benzyl, phenethyl, α-naphthyl methyl, and β-naphthyl methyl groups. A benzyl group and a phenethyl group are preferable.

The aliphatic acyl group as $R^8$ to $R^{15}$ may be a straight-chain group or a branched-chain group, and may optionally include an unsaturated bond. The aliphatic acyl group as $R^8$ to $R^{15}$ is preferably a straight-chain saturated aliphatic acyl group. The number of carbon atoms in the aliphatic acyl group as $R^8$ to $R^{15}$ is preferably 2 to 6, more preferably 2 to 4, and particularly preferably 2 or 3. Examples of suitable aliphatic acyl groups as $R^8$ to $R^{15}$ include acetyl, propionyl, n-butanoyl, n-pentanoyl, n-hexanoyl, n-heptanoyl, n-octanoyl, n-nonanoyl, and n-decanoyl groups. An acetyl group, a propionyl group, an n-butanoyl group, an n-pentanoyl group, and an n-hexanoyl group are preferable, and an acetyl group and a propionyl are more preferable.

The number of carbon atoms in the aromatic acyl group as $R^8$ to $R^{15}$ is 7 to 11. Examples of suitable aromatic acyl groups as $R^8$ to $R^{15}$ include benzoyl, α-naphthoyl, and β-naphthoyl groups. A benzoyl group is more preferable.

Specific examples of suitable compounds represented by the formula (a1-1) include the following compounds.

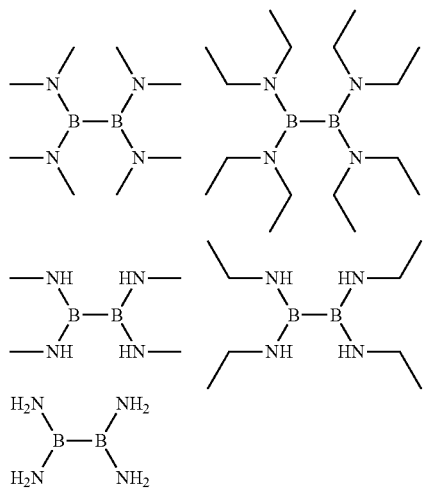

Examples of the other suitable compounds represented by the formula (a1) include a compound represented by the following formula (a1-2):

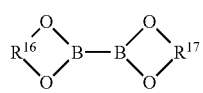

(a1-2)

(in the formula (a1-2), $R^{16}$ and $R^{17}$ each represents a divalent organic group).

Examples of the divalent organic groups as $R^{16}$ and $R^{17}$ include a group represented by $-R^{18}-NR^{20}-R^{19}-$, or a group derived from tartaric acid amide. The group derived from tartaric acid amide is a divalent group in which two hydroxyl groups are removed from the tartaric acid amide compound. $R^{18}$ and $R^{19}$ each independently represent an alkylene group having 1 to 6 carbon atoms, and a methylene group or an ethane-1,2-diyl group are preferable. $R^{20}$ represents a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms. Specific examples thereof are the same as the specific examples described for $R^8$ to $R^{15}$.

When $R^{16}$ and $R^{17}$ in the formula (a1-2) are groups derived from tartaric acid amide, specific examples of compounds represented by the formula (a1-2) include the group represented by the following formula (a1-2-1):

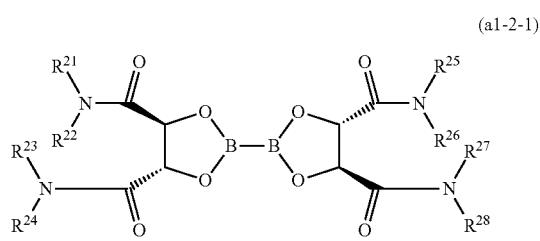

(a1-2-1)

(in the formula (a1-2-1), $R^{21}$ to $R^{28}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms).

Specific examples of the hydrogen atom, the aliphatic hydrocarbon group having 1 to 10 carbon atoms, the aromatic hydrocarbon group having 6 to 10 carbon atoms, the aralkyl group having 7 to 12 carbon atoms, the aliphatic acyl group having 2 to 10 carbon atoms, and the aromatic acyl group having 7 to 11 carbon atoms for $R^{21}$ to $R^{28}$ are the same as the specific examples of $R^8$ to $R^{15}$.

Specific examples of suitable compounds represented by the formula (a1-2-1) include the following compounds.

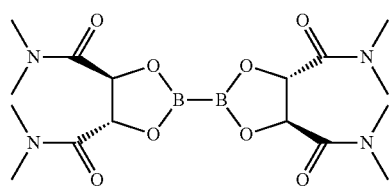

Specific examples of suitable compounds represented by the formula (a2) include a compound represented by the following formula (a2-1):

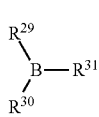
(a2-1)

(in the formula (a2-1), $R^{29}$ represents a nitrogen-containing heterocyclic group or a cyclic group which does not contain a nitrogen atom substituted with a nitrogen-containing group; $R^{30}$ and $R^{31}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms; $R^{30}$ and $R^{31}$ may be bonded to each other to form a ring).

$R^{29}$ is a nitrogen-containing heterocyclic group which may be substituted with a nitrogen-containing group, or a cyclic group which does not contain a nitrogen atom substituted with a nitrogen-containing group. In other words, $R^{29}$ is a cyclic group which essentially contains a nitrogen atom.

The nitrogen-containing heterocyclic group as $R^{29}$ may be a nitrogen-containing aromatic heterocyclic group or a nitrogen-containing aliphatic heterocyclic group. The nitrogen-containing heterocyclic group is a monovalent group in which one hydrogen atom is removed from various nitrogen-containing heterocycles. The hydrogen atom removed from the nitrogen-containing heterocycle may be bonded to any atoms constituting a ring, and may be bonded to a carbon atom, or a nitrogen atom, or a heteroatom other than a nitrogen atom.

Examples of suitable nitrogen-containing aromatic heterocycles giving a nitrogen-containing heterocyclic group include pyrrole, oxazole, isoxazole, oxadiazole, triazole, isothiazole, thiadiazole, imidazole, pyrazole, triazole, pyridine, pyrazine, pyrimidine, pyridazine, triazine, tetrazine, pentazine, indole, isoindole, indolizine, benzimidazole, benzotriazole, benzoxazole, benzothiazole, carbazole, purine, quinoline, isoquinoline, quinazoline, phthalazine, cinnoline and quinoxaline, and the like. Examples of suitable nitrogen-containing aliphatic heterocycles giving a nitrogen-containing heterocyclic group include pyrrolidine, pyrazolidine, triazolidine, pyrroline, pyrazoline, imidazoline, triazoline, piperidine, piperazine, triazinane, tetrazinane, pentazinane, morpholine, thiomorpholine, ε-caprolactam, δ-valerolactam, γ-butyrolactam, 2-imidazolidinone, phthalimide, s-triazine-2,4,6-trione, and the like.

When $R^{29}$ is a cyclic group which does not contain a nitrogen atom substituted with a nitrogen-containing group, the cyclic group may be an aromatic group or an aliphatic cyclic group, and may be a heterocyclic group containing a heteroatom other than a nitrogen atom. The cyclic group is preferably an aromatic group, more preferably a phenyl group, a naphthyl group, and a biphenylyl group, and further preferably a phenyl group.

When $R^{29}$ is a cyclic group which does not contain a nitrogen atom substituted with a nitrogen-containing group, examples of suitable nitrogen-containing groups as a substituent include a nitro group, an isocyanate group, an amino group represented by —$NR^{31}R^{32}$ or a substituted amino group, and a carbamoyl group represented by —CONH—$R^{33}$ or a substituted carbamoyl group. Furthermore, a group represented by the following formula, which includes a boron atom and a nitrogen atom, is preferable as a nitrogen-containing group.

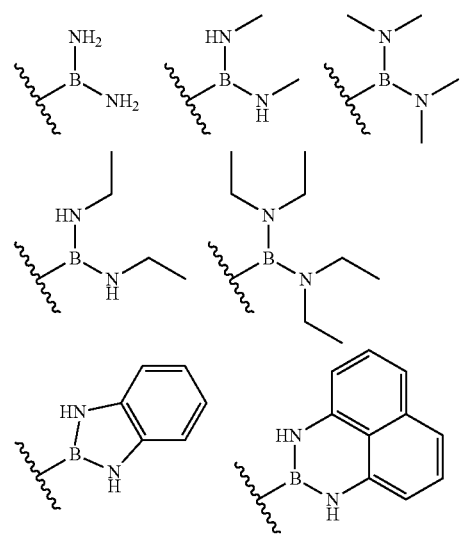

In the amino group represented by —$NR^{31}R^{32}$ or the substituted amino group, examples of suitable $R^{31}$ and $R^{32}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms. $R^{31}$ and $R^{32}$ may be bonded to each other to form a ring. Specific examples of these groups are the same as those described for $R^8$ to $R^{15}$.

In the carbamoyl group represented by —CONH—$R^{33}$ or a substituted carbamoyl group, examples of suitable $R^{32}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms. Specific examples of these groups are the same as those described for $R^8$ to $R^{15}$.

Among the above-described nitrogen-containing groups, a nitro group, an amino group, a dimethyl amino group, a diethyl amino group, a diphenyl amino group, a phenyl amino group, a carbamoyl group, and an isocyanate group are preferable, and a nitro group and an amino group are more preferable.

When $R^{29}$ is a cyclic group which does not contain a nitrogen atom substituted with a nitrogen-containing group, the number of nitrogen-containing groups on the cyclic group is not particularly limited. The number of nitrogen-containing groups on the cyclic group is preferably 1 to 4, more preferably 1 or 2, and particularly preferably 1.

Specific examples of suitable compounds represented by the formula (a2-1) include the following compounds.

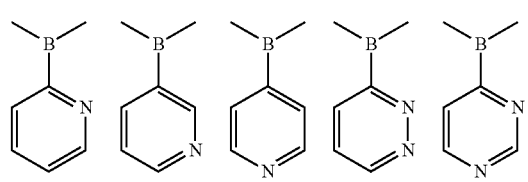

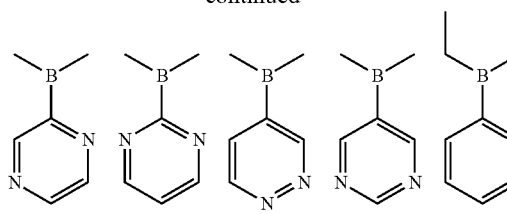
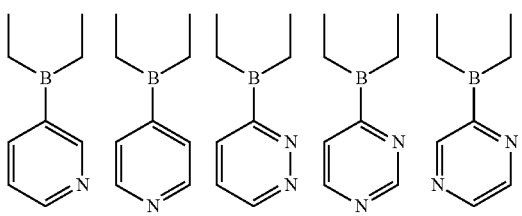
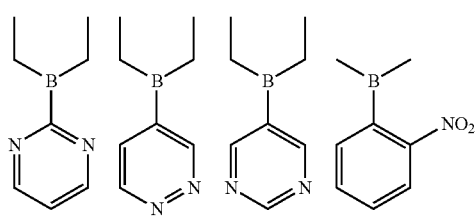
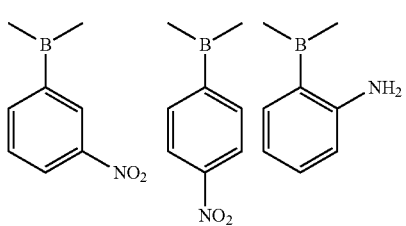
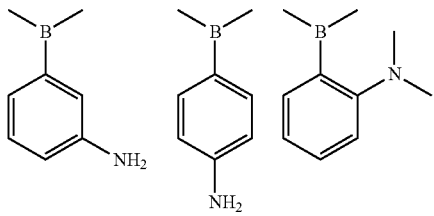
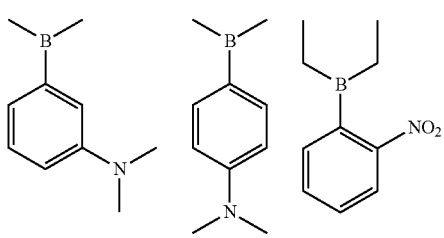
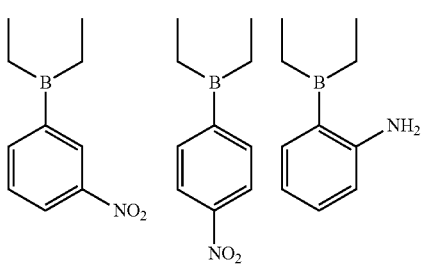

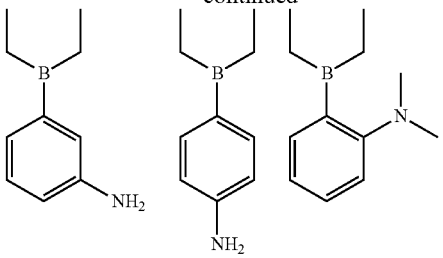
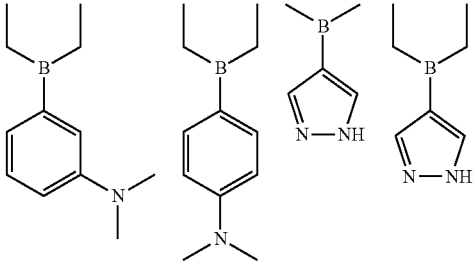

Specific examples of other suitable compounds represented by the formula (a2) include a compound represented by the following formula (a2-2):

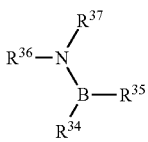

(a2-2)

(in the formula (a2-2), $R^{34}$ and $R^{35}$ each independently represent a hydrogen atom, a hydroxyl group, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms; and $R^{36}$ and $R^{37}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms; $R^{34}$ and $R^{35}$ may be bonded to each other to form a ring; $R^{34}$ and $R^{36}$ may be bonded to each other to form a ring; $R^{35}$ and $R^{37}$ may be bonded to each other to form a ring; and $R^{36}$ and $R^{37}$ may be bonded to each other to form a ring).

When $R^{34}$, $R^{35}$, $R^{36}$, and $R^{37}$ are an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms, specific examples of these groups are the same as those described for $R^8$ to $R^{18}$.

$R^{34}$ and $R^{35}$ are preferably a hydrogen atom. $R^{36}$ and $R^{37}$ are preferably an aliphatic hydrocarbon group having 1 to 10 carbon atoms, more preferably an alkyl group having 1 to 10 carbon atoms, further preferably alkyl groups having 1 to 6 carbon atoms, and particularly preferably an alkyl group having 1 to 3 carbon atoms.

When $R^{34}$ and $R^{36}$ are bonded to each other to form a ring, or $R^{35}$ and $R^{37}$ are bonded to each other to form a ring, a divalent group formed by $R^{34}$ and $R^{36}$ or $R^{35}$ and $R^{37}$ is preferably, for example, an alkylene group. Preferable examples of the alkylene group include a trimethylene group or a tetramethylene group. In other words, it is preferable that $R^{34}$ and $R^{36}$ or $R^{35}$ and $R^{37}$, together with a boron atom and a nitrogen atom, form a saturated aliphatic five-membered ring or a saturated aliphatic six-membered ring.

Specific examples of suitable compounds represented by the formula (a2-2) include the following compounds.

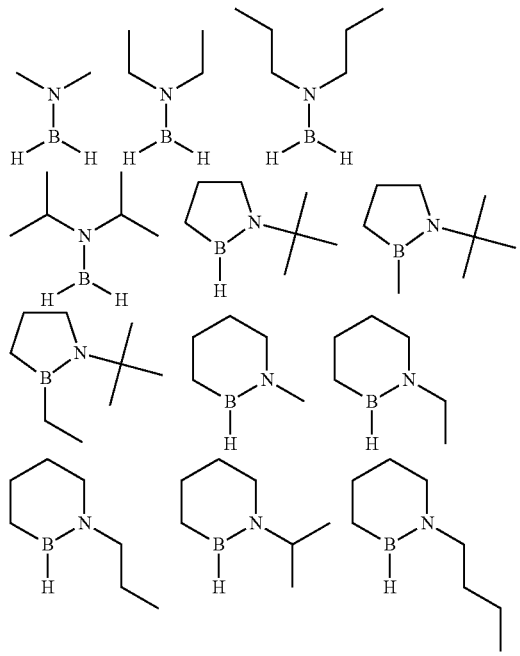

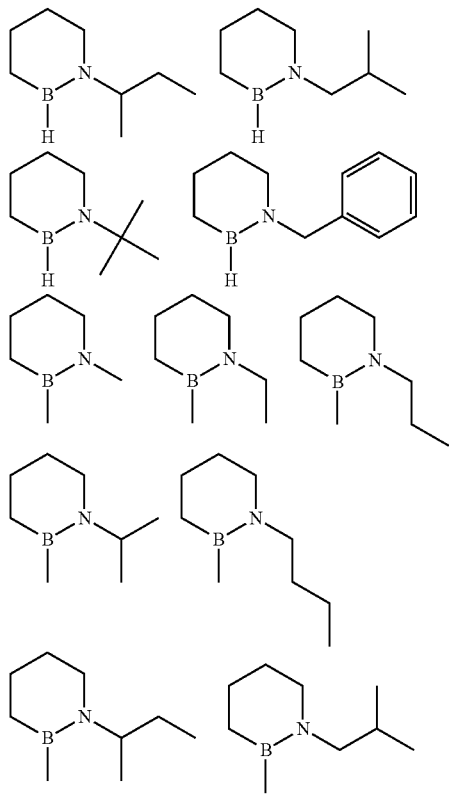

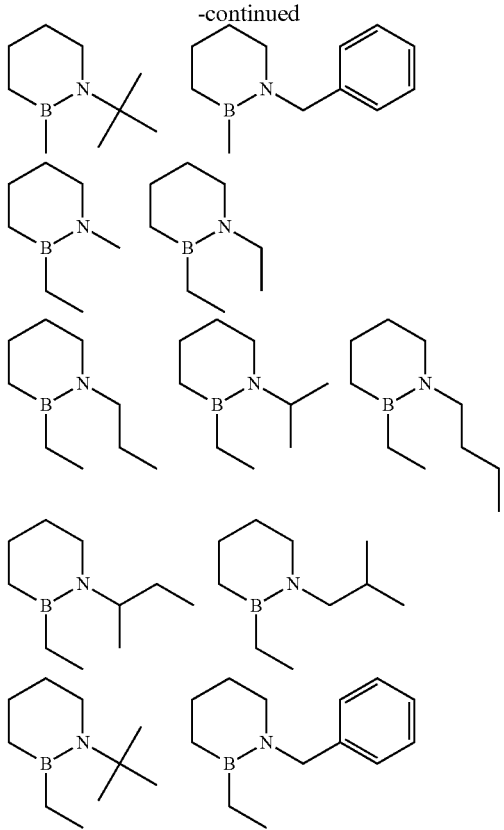

Specific examples of other suitable compounds represented by the formula (a2) include a compound represented by the following formula (a2-3):

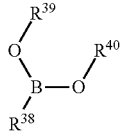

(a2-3)

(in the formula (a2-3), $R^{38}$ represents a nitrogen-containing heterocyclic group or a cyclic group which does not contain a nitrogen atom substituted with a nitrogen-containing group; $R^{39}$ and $R^{40}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms;

$R^{39}$ and $R^{40}$ may be bonded to each other to form a ring).

Examples of the nitrogen-containing heterocyclic group or the cyclic group which does not contain a nitrogen atom substituted with a nitrogen-containing group as $R^{38}$ are the same as those described for $R^{29}$ in the formula (a2-1). $R^{39}$ and $R^{40}$ are an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms, specific examples of these groups are the same as those described for $R^8$ to $R^{15}$.

Among the compounds represented by the formula (a2-3), a compound in which —OR$^{39}$ and —OR$^{40}$ form the following structures are preferable.
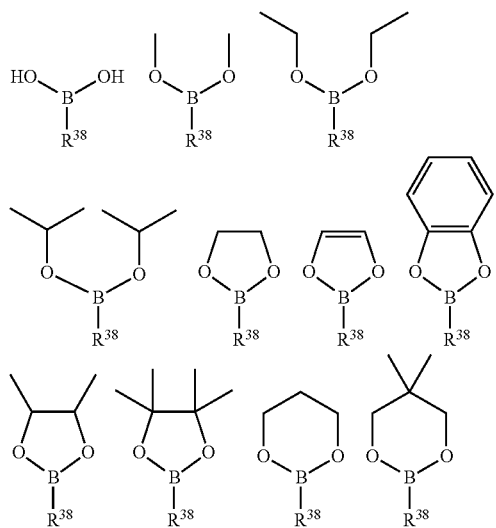
Specific examples of suitable compounds represented by the formula (a2-3) include the following compounds.
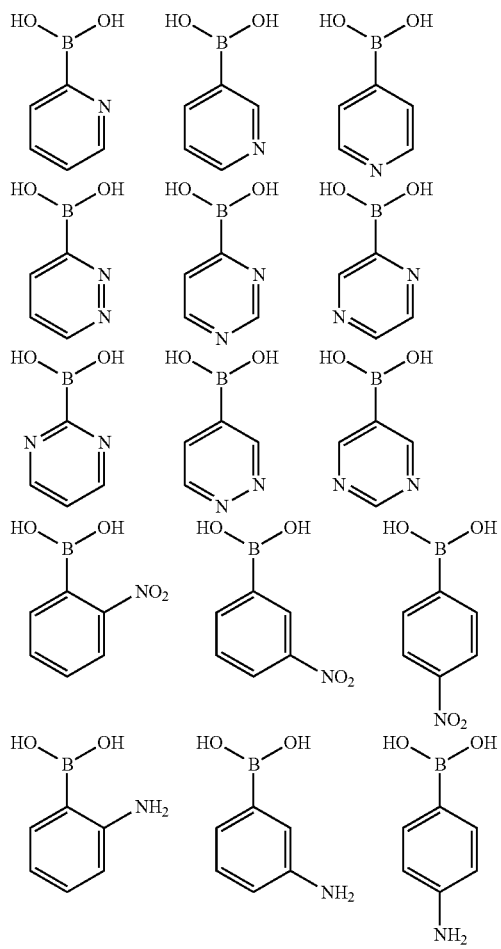
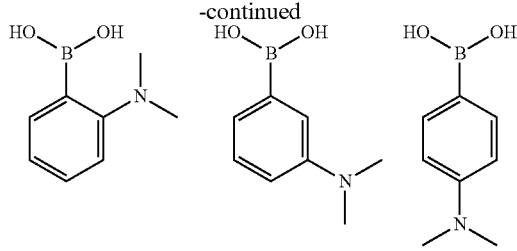
-continued
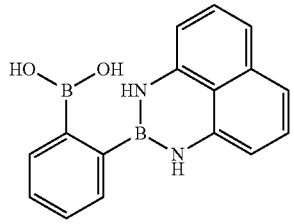
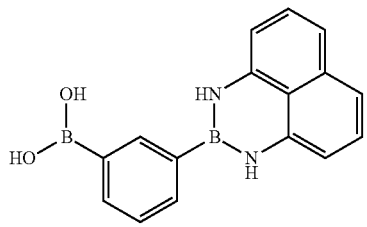
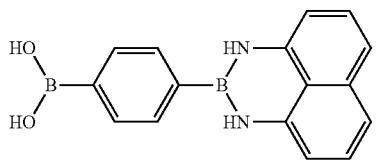
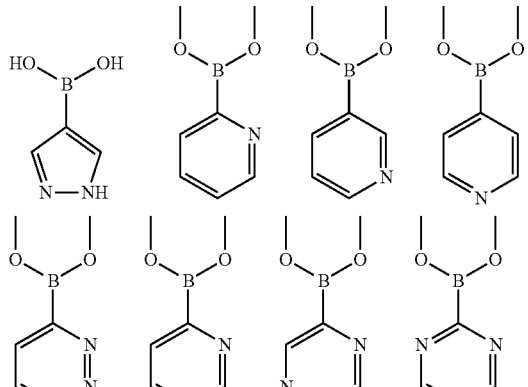

-continued
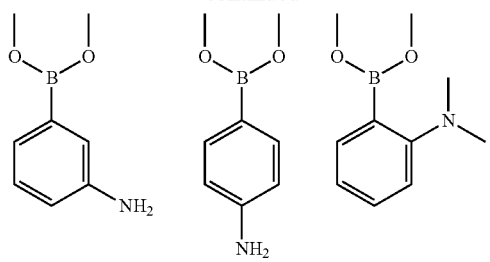
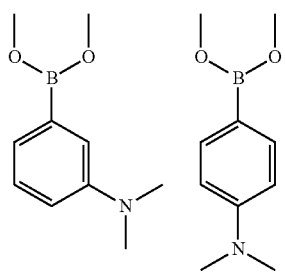
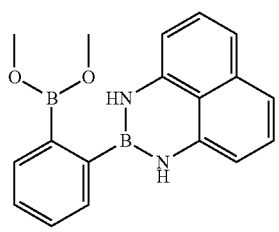
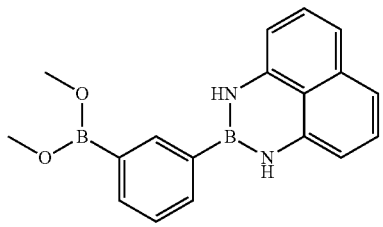
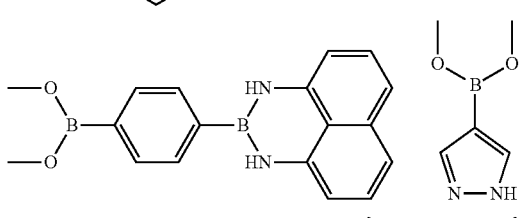
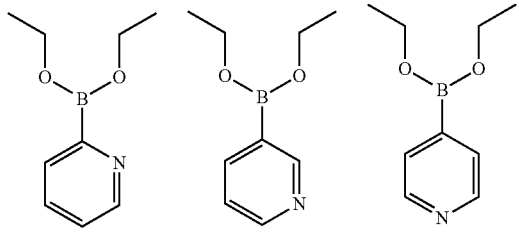
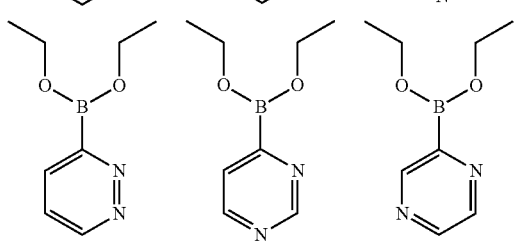
-continued
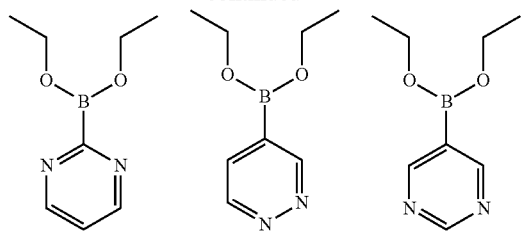
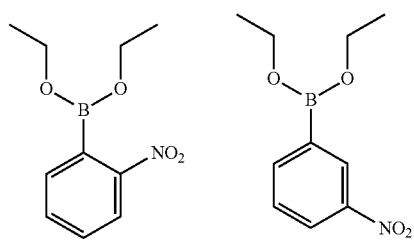
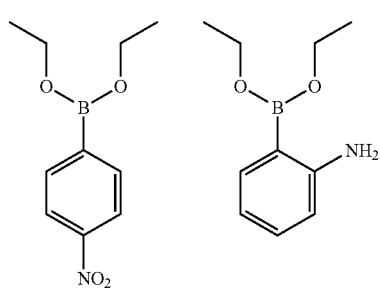
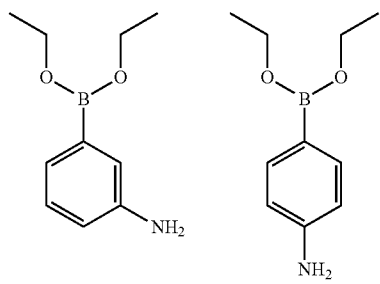
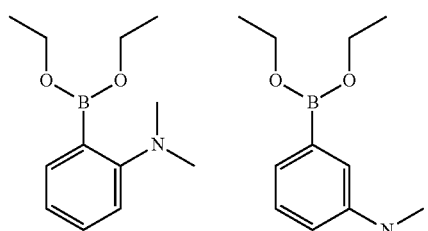
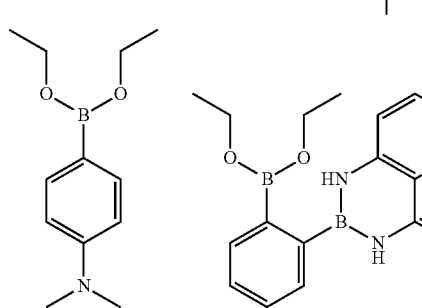

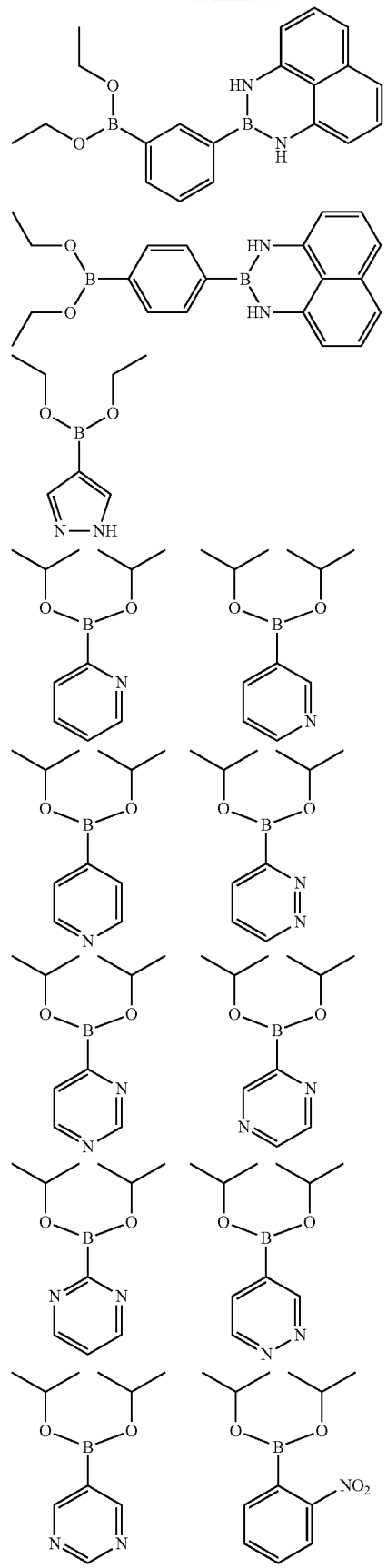
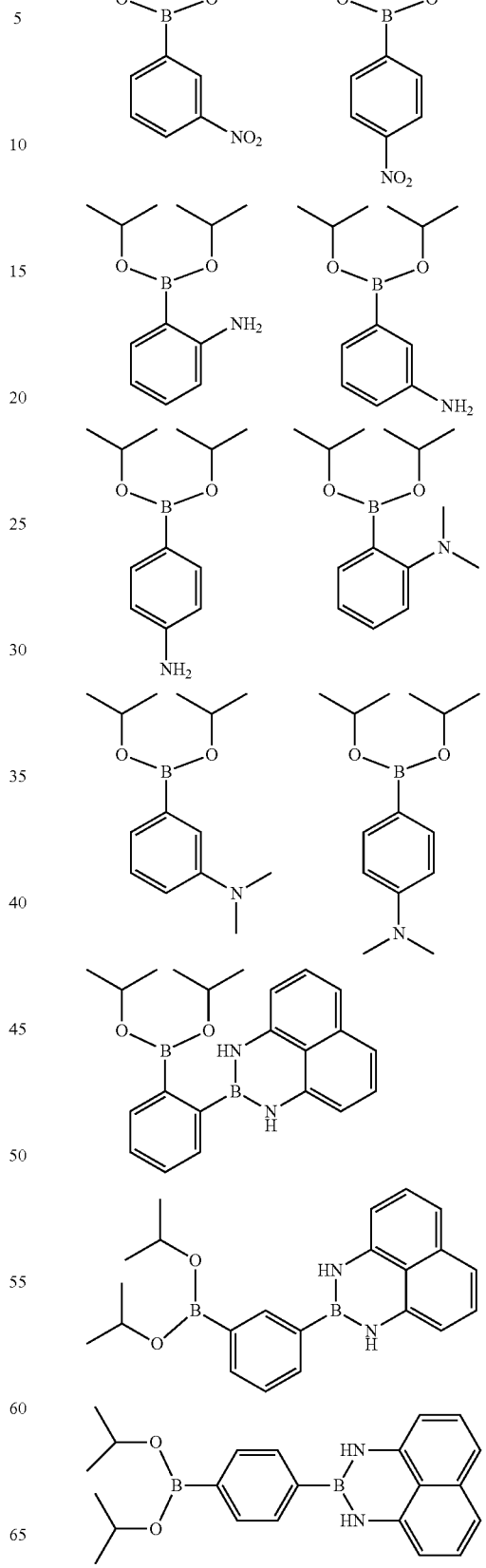

-continued
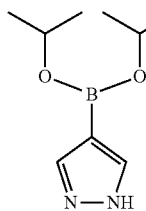
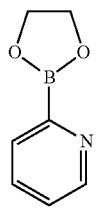 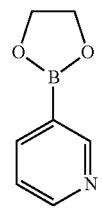 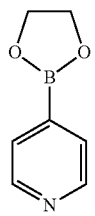
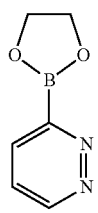 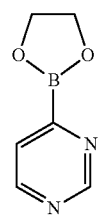 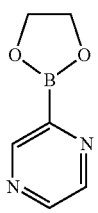
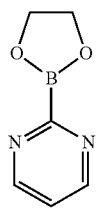 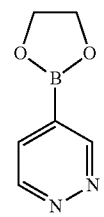 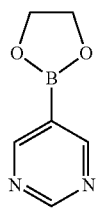
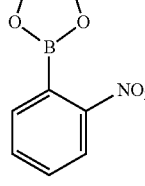 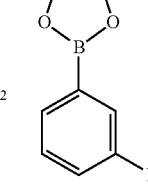 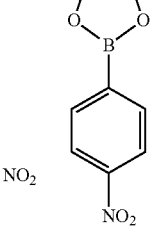
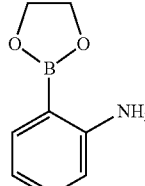 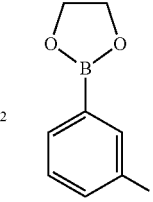 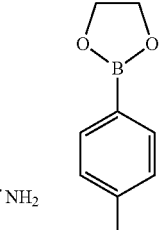
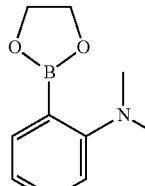 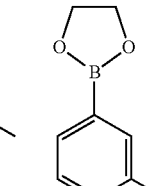 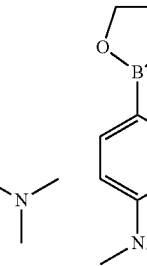
-continued
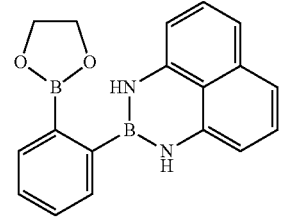
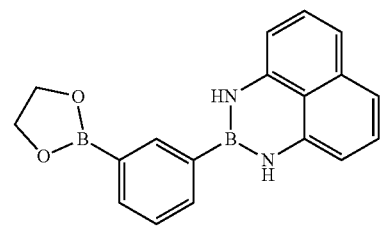
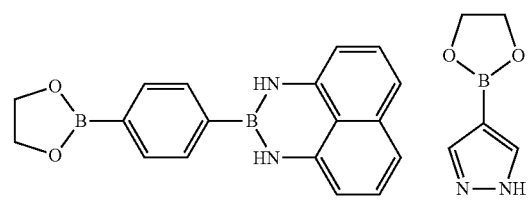
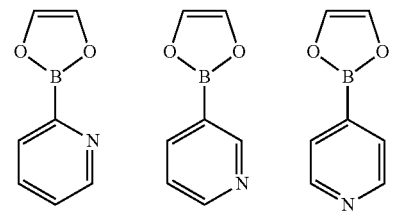
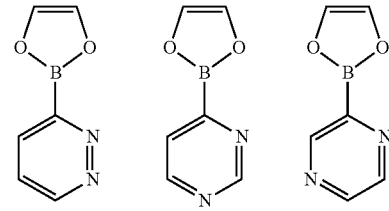
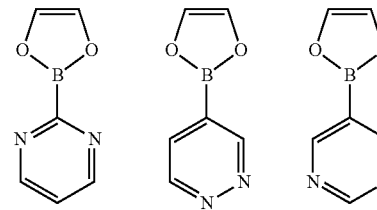
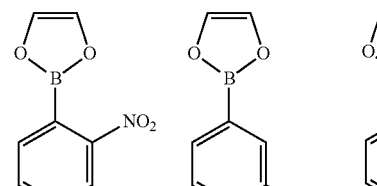

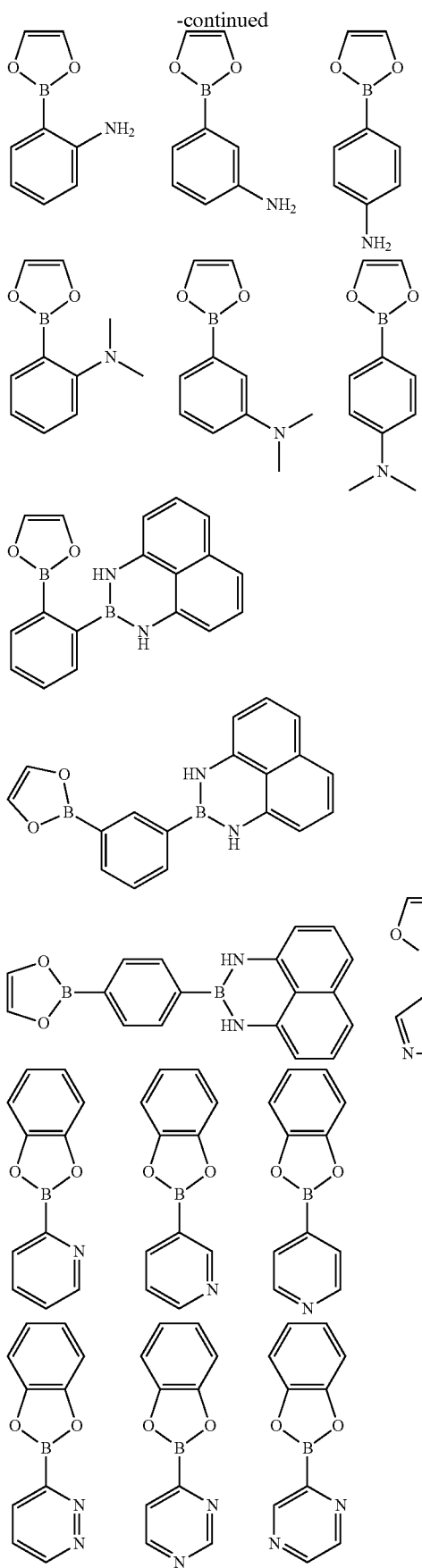
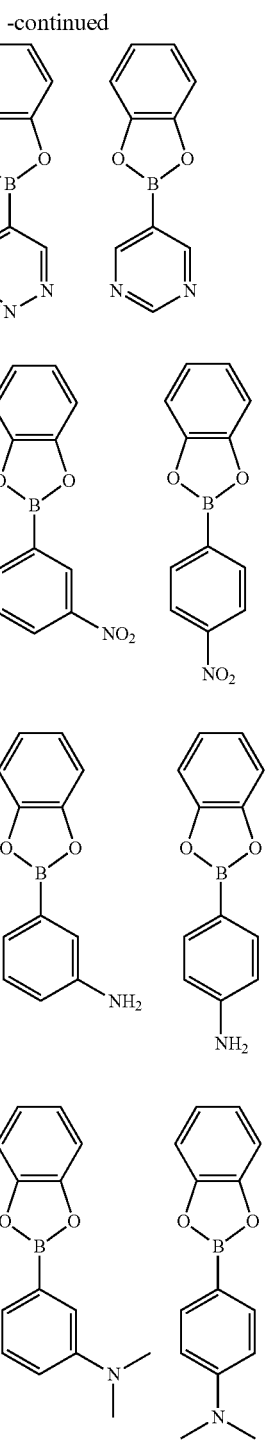

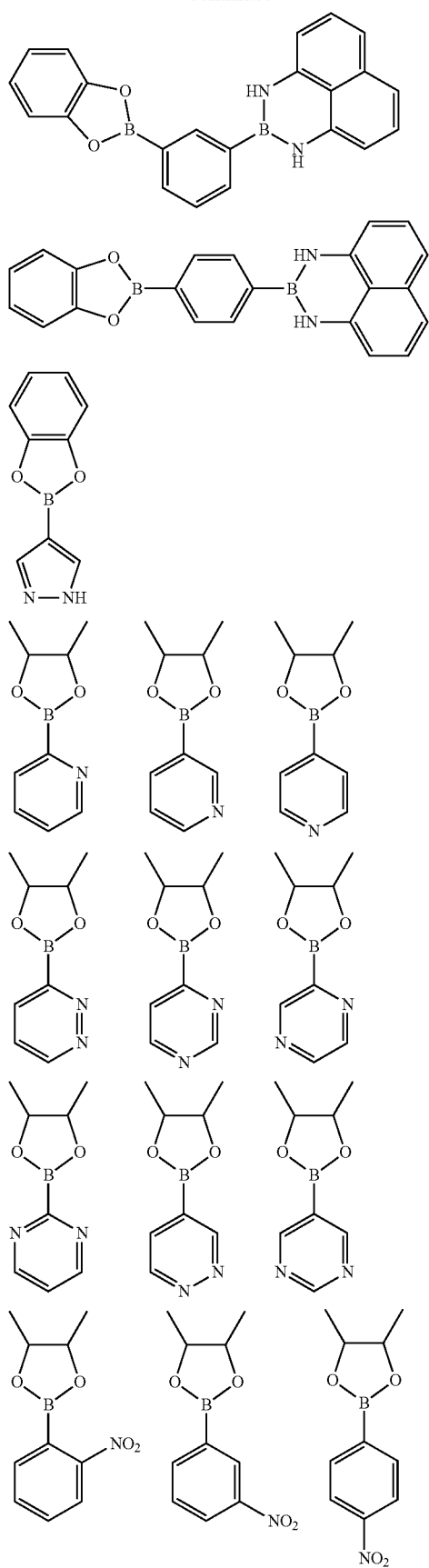
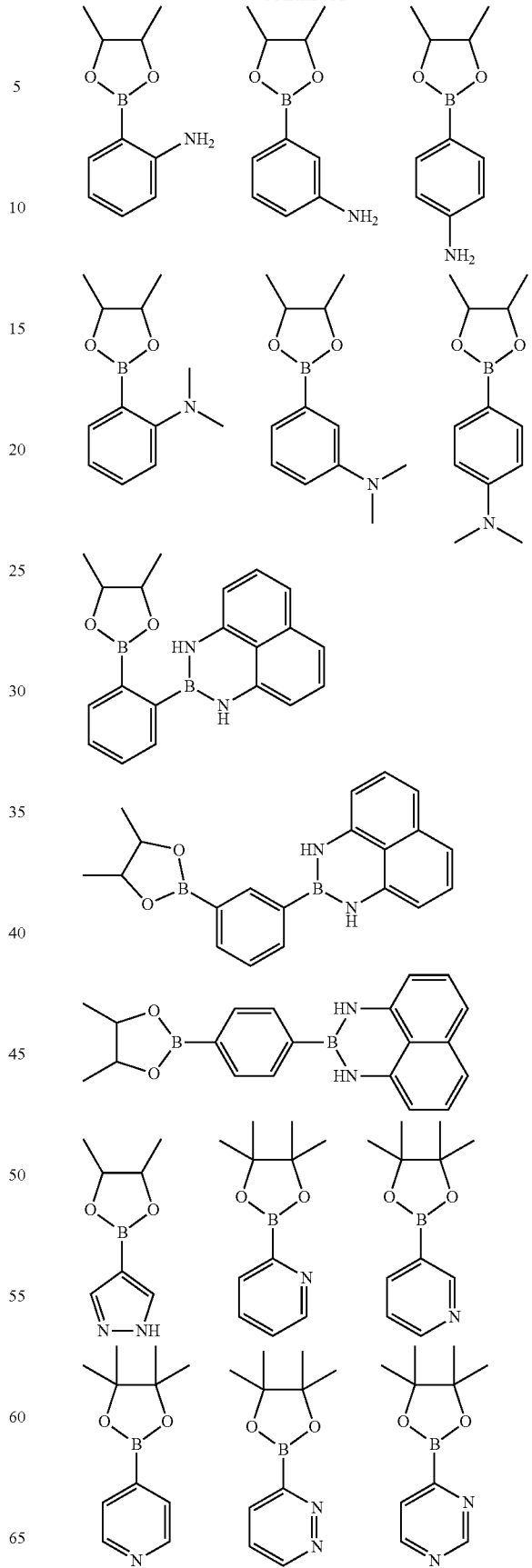

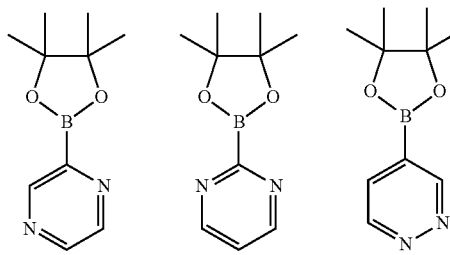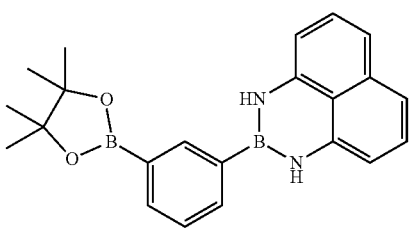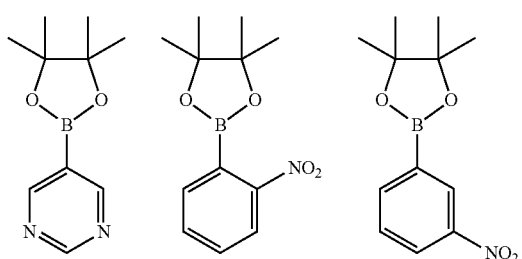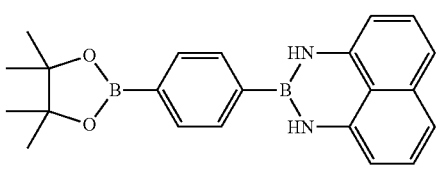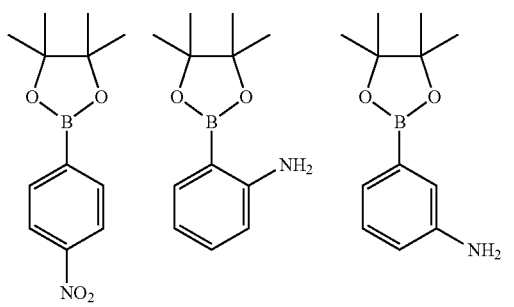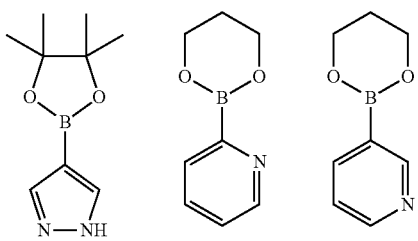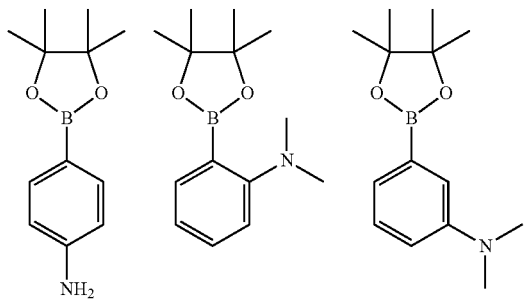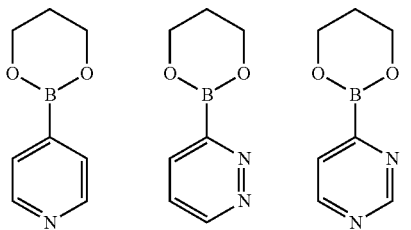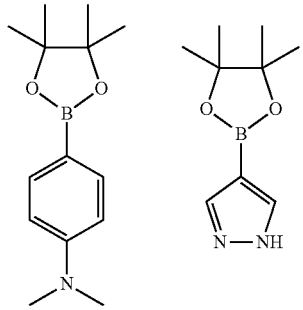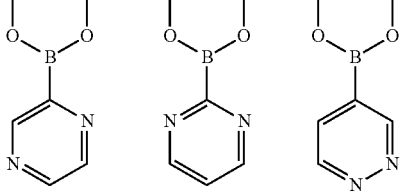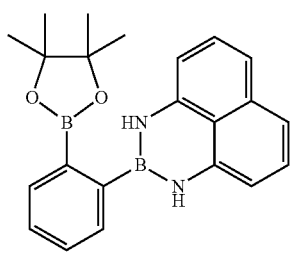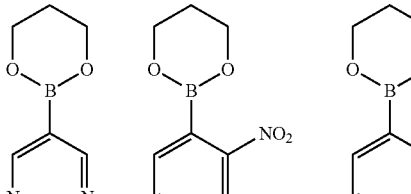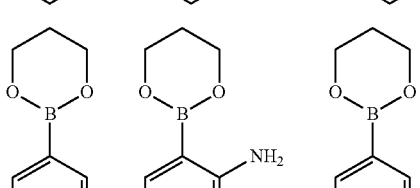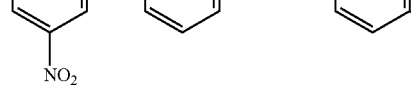

-continued
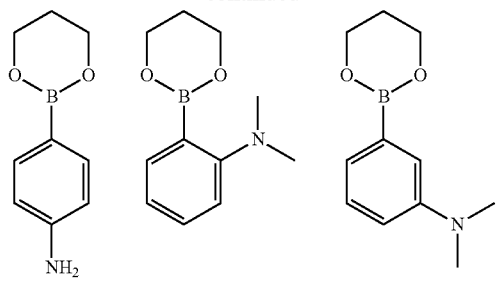
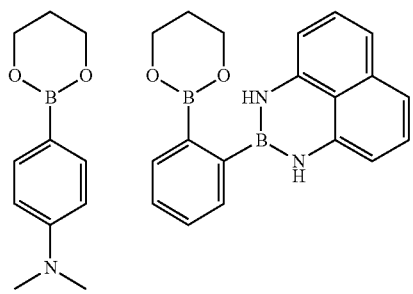
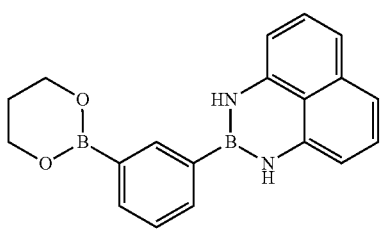
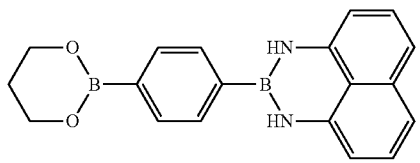
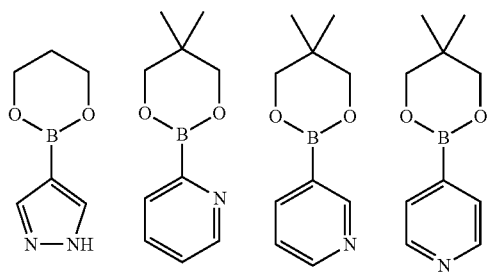
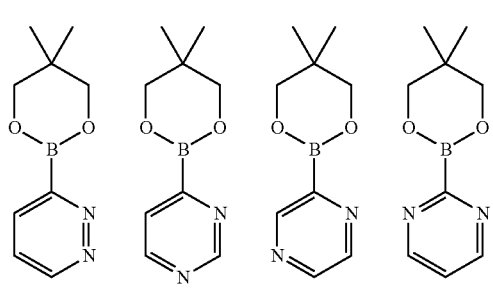
-continued
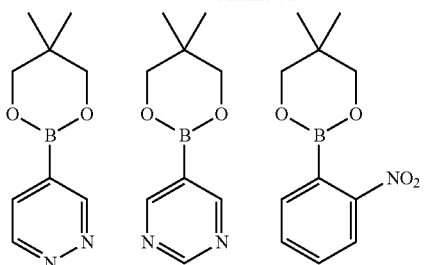
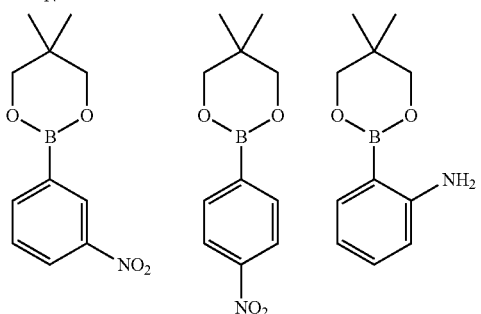
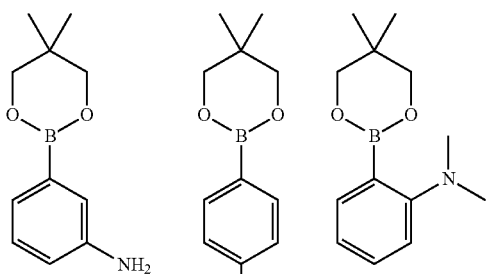
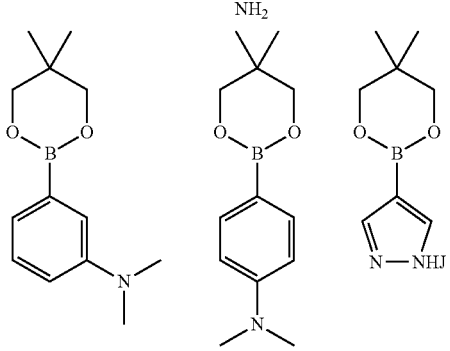
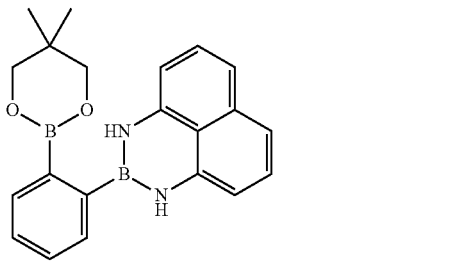
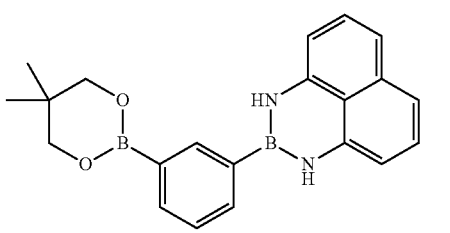

-continued

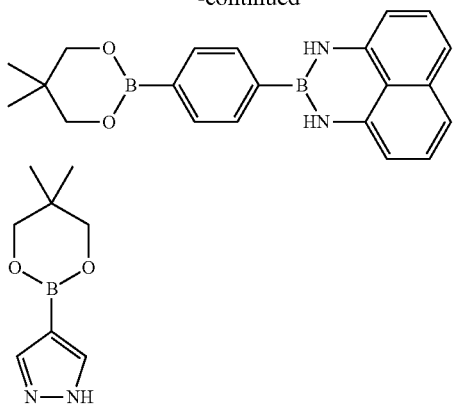

Specific examples of the other suitable compounds represented by the formula (a2) include a compound represented by the following formula (a2-4):

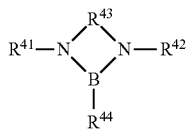

(a2-4)

(in the formula (a2-4), $R^{41}$ and $R^{42}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms. $R^{43}$ represents an alkylene group having 1 to 10 carbon atoms,
—$BR^{45}$—, —$BR^{46}$—$BR^{46}$—,
—$BR^{45}$—$NR^{46}$—,
—$NR^{46}$—$NR^{46}$—,
—$BR^{45}$—$NR^{46}$—$BR^{45}$—, or
—$BR^{46}$—$NR^{46}$—$BR^{46}$—$NR^{46}$—$BR^{46}$—. $R^{46}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms. $R^{44}$ and $R^{45}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, and an aromatic acyl group having 7 to 11, a nitrogen-containing heterocyclic group, or a cyclic group which does not contain a nitrogen atom substituted with a nitrogen-containing group).

When $R^{41}$, $R^{42}$, $R^{44}$, $R^{45}$, and $R^{46}$ are an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms, specific examples of these groups are the same as those described for $R^8$ to $R^{15}$. When $R^{44}$ and $R^{45}$ are a nitrogen-containing heterocyclic group, or a cyclic group which does not contain a nitrogen atom substituted with a nitrogen-containing group, specific examples of these groups are the same as those described for $R^{29}$.

Among compounds represented by the formula (a2-4), compounds represented by the following formula (a2-4-1) to (a2-4-8) are preferable.

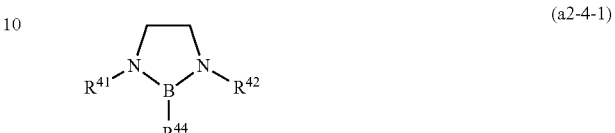

(a2-4-1)

(a2-4-2)

(a2-4-3)

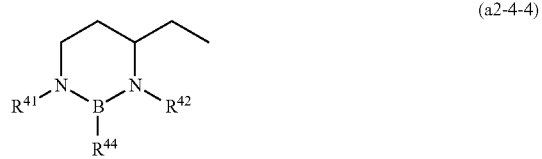

(a2-4-4)

(a2-4-5)

(a2-4-6)

(a2-4-7)

(a2-4-8)

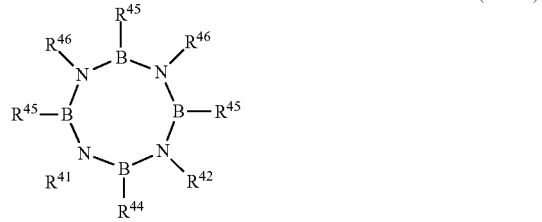

Preferable examples of compound represented by the formula (a2-4-6) include a compound represented by the following formula.
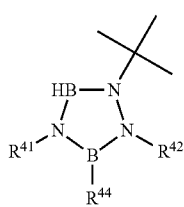 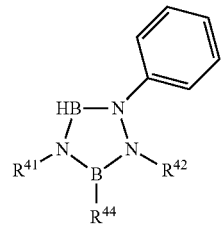
Preferable examples of compounds represented by the formula (a2-4-7) include compounds represented by the following formulae.
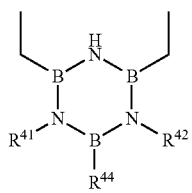 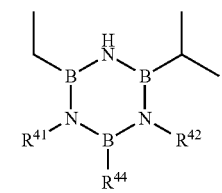
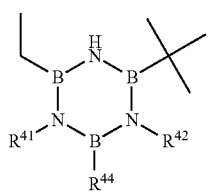 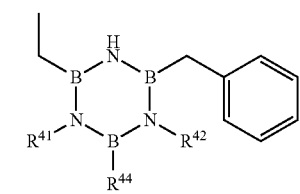
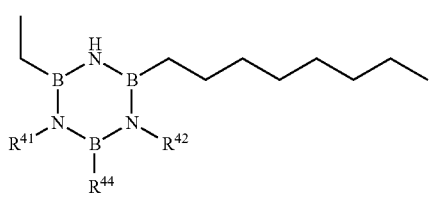
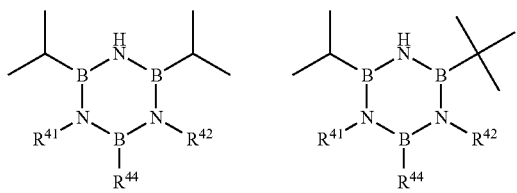
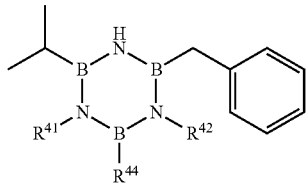
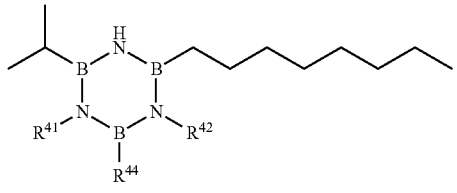
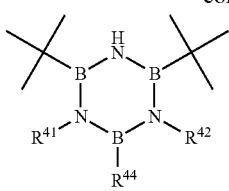
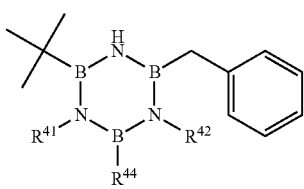
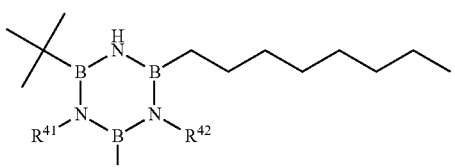
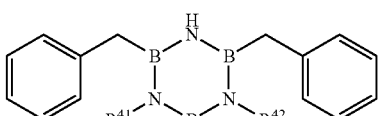
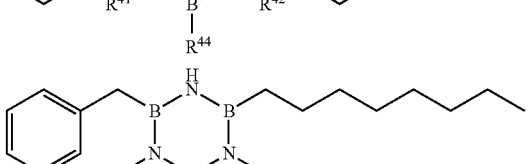
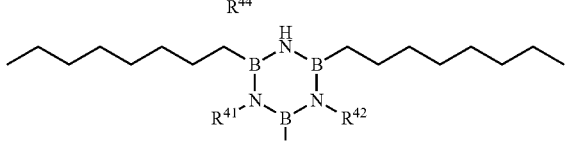
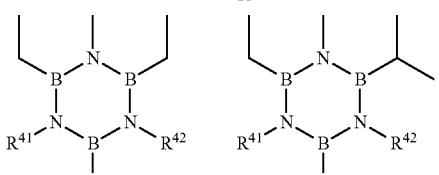
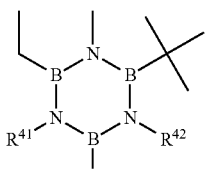
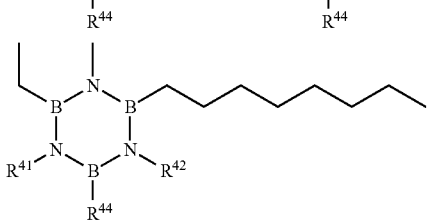

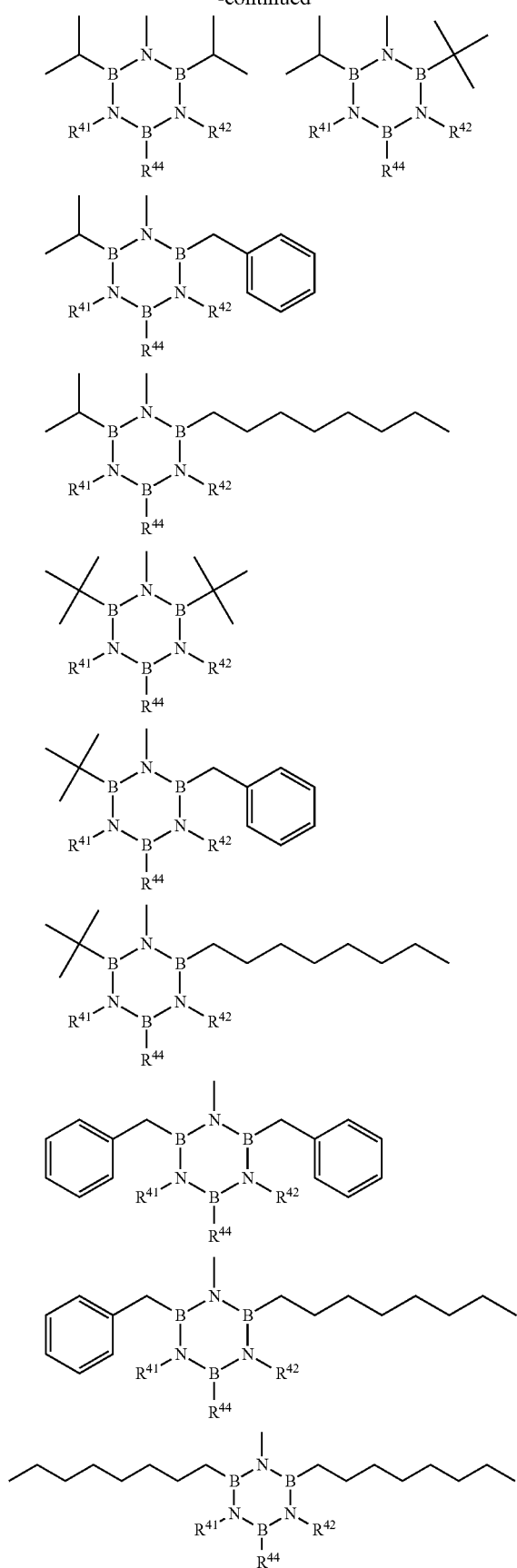
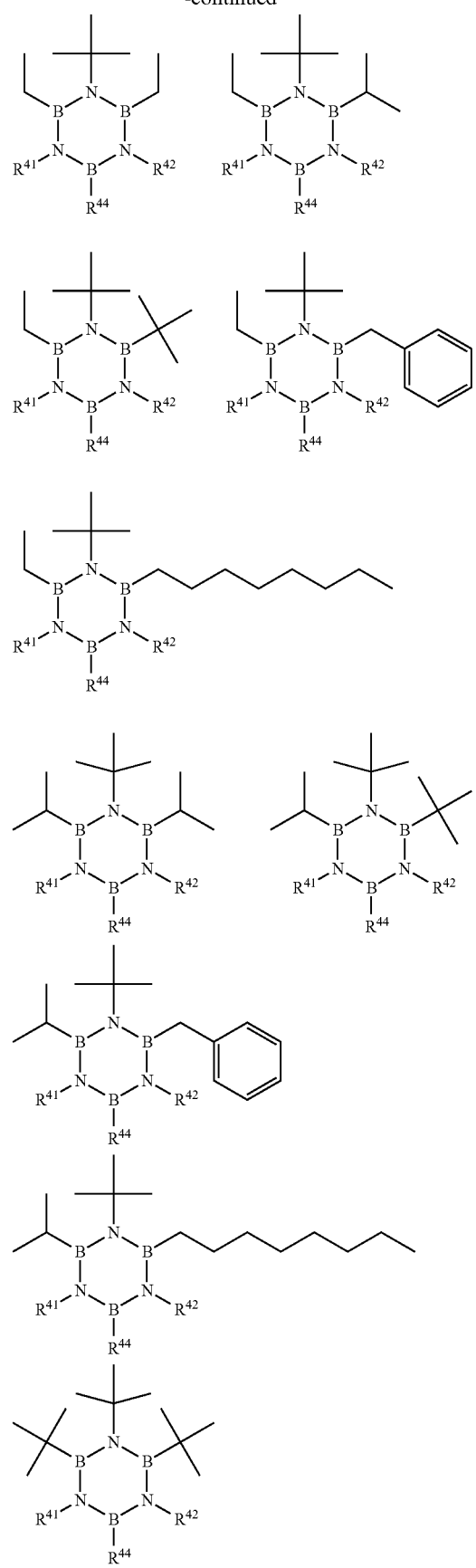

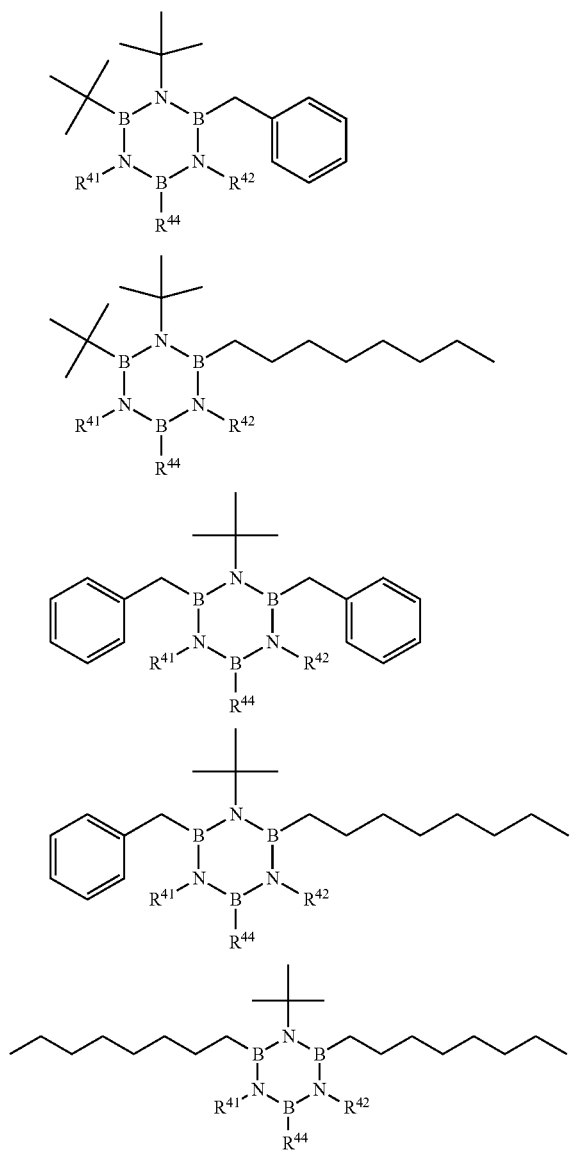
Specific examples of suitable compounds represented by the formula (a2-4) include the following compounds.
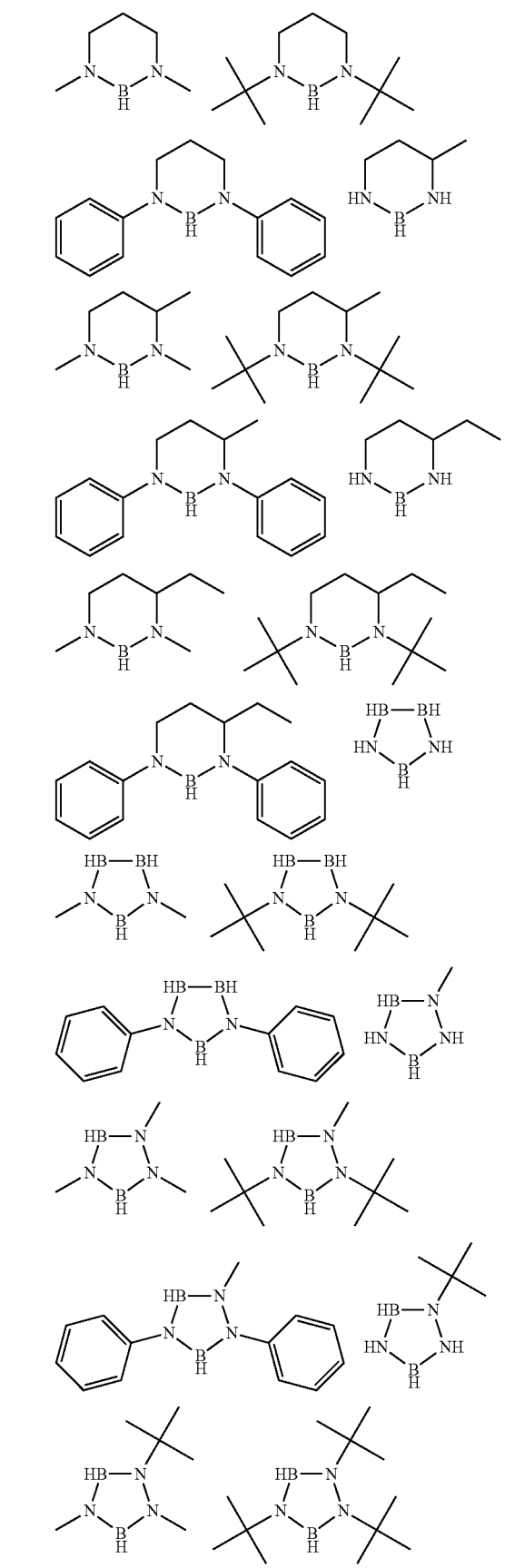

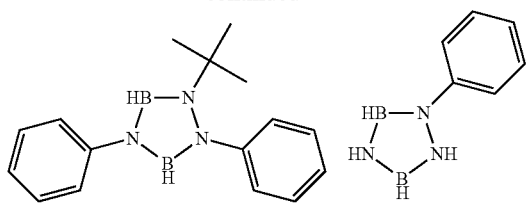
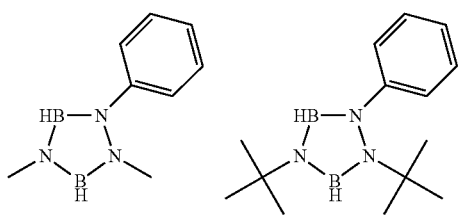
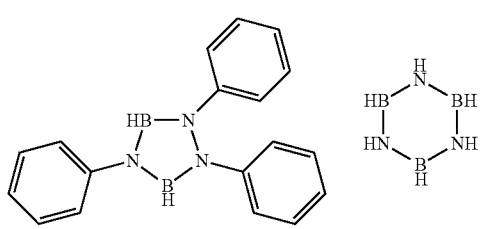
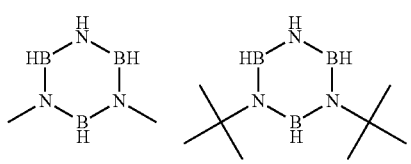
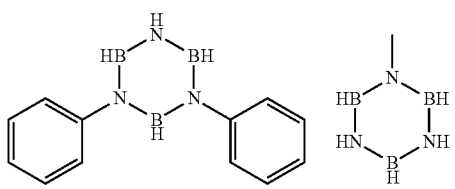
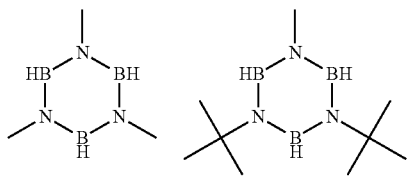
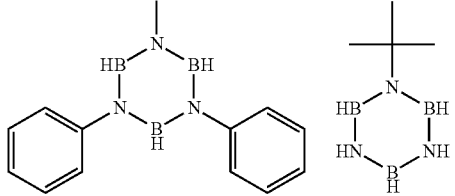
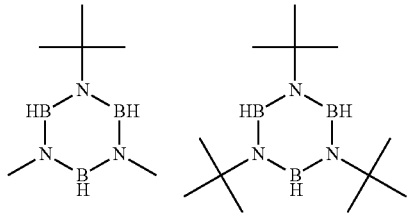

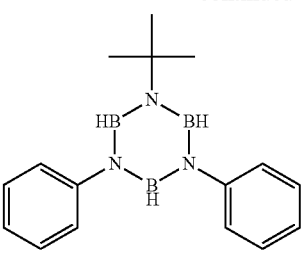

Examples of the other suitable compounds represented by the formula (a2) include a compound represented by the following formula (a2-5):

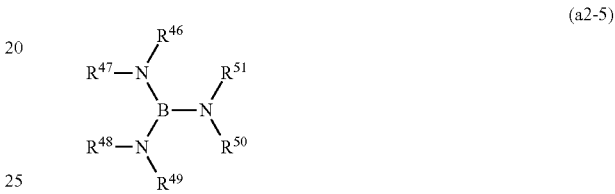

(a2-5)

(in the formula (a2-5), $R^{46}$ to $R^{51}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms. $R^{46}$ and $R^{47}$ and, $R^{48}$ and $R^{49}$, and $R^{50}$ and $R^{51}$ each independently may be bonded to each other to form a ring).

When $R^{46}$ to $R^{51}$ are an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms, specific examples of these groups are the same as those described for $R^8$ to $R^{15}$.

Specific examples of suitable compounds represented by the formula (a2-5) include the following compounds.

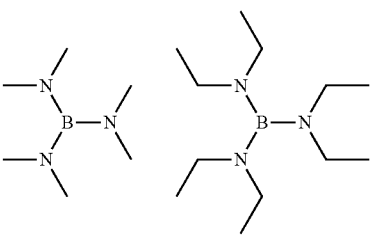

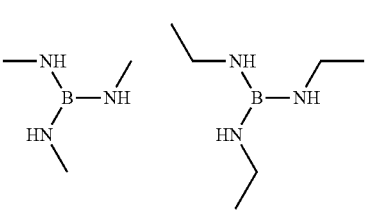

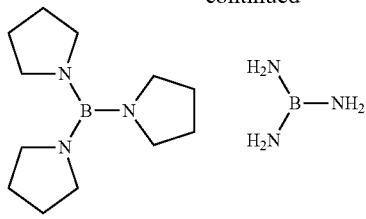

The content of the impurity diffusion component (A) in the diffusion agent composition is not particularly limited. The content of the impurity diffusion component (A) in the diffusion agent composition is preferably 0.01 to 20 mass %, more preferably 0.05 to 15 mass %, and particularly preferably 0.1 to 10 mass %.

[Hydrolyzable Silane Compound (B)]

The diffusion agent composition may contain a hydrolyzable silane compound (B). When the diffusion agent composition contains a hydrolyzable silane compound (B), when the diffusion agent composition is applied onto a semiconductor substrate to form a thin film, the hydrolyzable silane compound is subjected to hydrolysis condensation to form a silicon oxide-based very thin film within the coating film. When the silicon oxide-based very thin film is formed within the coating film, external diffusion of the impurity diffusion component (A) on the outside of the substrate is suppressed. In this case, even when the film of the diffusion agent composition is a thin film, the impurity diffusion component (A) is likely to be diffused well and uniformly into the semiconductor substrate.

The hydrolyzable silane compound (B) produces a hydroxyl group as a result of hydrolysis and has a functional group bondable to a Si atom. Functional groups that produce a hydroxyl group as a result of hydrolysis include alkoxy, isocyanate, and dimethylamino groups and halogen atoms. Straight-chain or branched-chain aliphatic alkoxy groups having 1 to 5 carbon atoms are preferred as the alkoxy group. Specific examples of suitable alkoxy groups include methoxy, ethoxy, n-propoxy, isopropoxy, and n-butoxy groups. Preferred halogen atoms are chlorine, fluorine, bromine, and iodine atoms, and the chlorine atom is more preferred.

The functional group that produces a hydroxyl group as a result of hydrolysis is preferably an isocyanate group and straight-chain or branched-chain aliphatic alkoxy group having 1 to 5 carbon atoms, more preferably methoxy, ethoxy, and isocyanate groups, from the viewpoints of rapid hydrolysis and handling property and easily availability of the hydrolyzable silane compound (B).

Specific examples of the hydrolyzable silane compound (B) having a straight-chain or branched-chain aliphatic alkoxy groups having 1 to 5 carbon atoms include tetramethoxysilane, tetraethoxysilane, tetra-n-propoxysilane, tetraisopropoxysilane, tetra-n-butoxysilane, tetra-n-pentyloxysilane, trimethoxymonoethoxysilane, dimethoxydiethoxysilane, monomethoxytriethoxysilane, trimethoxymono-n-propoxysilane, dimethoxydi-n-propoxysilane, monomethoxytri-n-propoxysilane, trimethoxy mono-n-butoxysilane, dimethoxydi-n-butoxysilane, monomethoxytri-n-tributoxysilane, trimethoxymono-n-pentyloxysilane, dimethoxydi-n-pentyloxysilane, monomethoxytri-n-pentyloxysilane, triethoxymono-n-propoxysilane, diethoxydi-n-propoxysilane, monoethoxytri-n-propoxysilane, triethoxymono-n-butoxysilane, diethoxydi-n-butoxysilane, monoethoxytri-n-butoxysilane, triethoxymono-n-pentyloxysilane, diethoxydi-n-pentyloxysilane, monoethoxytri-n-pentyloxysilane, tri-n-propoxymono-n-butoxysilane, di-n-propoxydi-n-butoxysilane, mono-n-propoxytri-n-propoxysilane, tri-n-propoxy mono-n-pentyloxysilane, di-n-propoxydi-n-pentyloxysilane, mono-n-propoxytri-n-pentyloxysilane, tri-n-butoxy mono-n-pentyloxysilane, di-n-butoxydi-n-pentyloxysilane, mono-n-butoxytri-n-pentyloxysilane, methyltrimethoxysilane, methyltriethoxysilane, methyltri-n-propoxysilane, methyltri-n-propoxysilane, methyltri-n-butoxysilane, methyltri-n-pentyloxysilane, ethyltrimethoxysilane, ethyltriethoxysilane, ethyltri-n-propoxysilane, ethyltri-n-butoxysilane, and ethyltri-n-pentyloxysilane. These hydrolyzable silane compounds (B) may be used alone or in a combination of two or more of these. Furthermore, partially hydrolyzed condensate of the alkoxysilane compounds may also be used as the hydrolyzable silane compound (B).

Among these, tetramethoxysilane, tetraethoxysilane, methyltrimethoxysilane, methyltriethoxysilane, ethyltrimethoxysilane, and ethyltriethoxysilane are preferred, and tetramethoxysilane and tetraethoxysilane are particularly preferred.

Compounds represented by the following formula (b1) are preferred as the isocyanate-group-containing hydrolyzable silane compound (B).

$$(R^{b1})_{4-n}Si(NCO)_n \quad (b1)$$

(in the formula (b1), $R^{b1}$ represents a hydrocarbon group; and n is an integer of 3 or 4).

The hydrocarbon group as $R^{b1}$ in the formula (b1) is not particularly limited as long as the object of the present invention is not impeded. Preferably, $R^{b1}$ represents an aliphatic hydrocarbon group having 1 to 12 carbon atoms, an aromatic hydrocarbon group having 1 to 12 carbon atoms, or an aralkyl group having 1 to 12 carbon atoms.

Examples of suitable aliphatic hydrocarbon groups having 1 to 12 carbon atoms include methyl, ethyl, n-propyl, isopropyl, n-butyl, sec-butyl, isobutyl, tert-butyl, n-pentyl, isopentyl, neopentyl, cyclopentyl, n-hexyl, cyclohexyl, n-heptyl, cycloheptyl, n-octyl, cyclooctyl, n-nonyl, n-decyl, n-undecyl, and n-dodecyl groups.

Examples of suitable aromatic hydrocarbon groups having 1 to 12 carbon atoms include phenyl, 2-methylphenyl, 3-methylphenyl, 4-methylphenyl, 2-ethylphenyl, 3-ethylphenyl, 4-ethylphenyl, α-naphthyl, β-naphthyl, and biphenylyl groups.

Examples of suitable aralkyl groups having 1 to 12 carbon atoms include benzyl, phenetyl, α-naphthylmethyl, β-naphthylmethyl, 2-α-naphthylethyl, and 2-β-naphthylethyl groups.

Among the above-described hydrocarbon atoms, methyl and ethyl groups are preferred, and a methyl group is more preferred.

Among the hydrolyzable silane compounds (B) represented by the formula (b1), tetraisocyanatesilane, methyltriisocyanatesilane, and ethyltriisocyanatesilane are preferred, and tetraisocyanatesilane is more preferred.

The hydrolyzable silane compound (B) containing an isocyanate group and the hydrolyzable silane compound (B) containing a straight-chain or branched-chain aliphatic alkoxy group having 1 to 5 carbon atoms may also be used in combination. In this case, the ratio X/Y between the number of moles X of the hydrolyzable silane compound (B) containing an isocyanate group and the number of moles Y of the hydrolyzable silane compound (B) containing a straight-chain or branched-chain aliphatic alkoxy group having 1 to 5 carbon atoms is preferably 1/99 to 99/1, more preferably 50/50 to 95/5, particularly preferably 60/40 to 90/10.

When the diffusion agent composition contains a hydrolyzable silane compound (B), the content of the hydrolyzable silane compound (B) in the diffusion agent composition is not particularly limited but it is preferably 0.001 to 3.0% by mass, more preferably 0.01 to 1.0% by mass, in terms of Si concentration. When the diffusion agent composition contains the hydrolyzable silane compound (B) at this concentration, external diffusion of the impurity diffusion component (A) from the thin coating film formed using the diffusion agent composition is easily suppressed well, and the impurity diffusion component is easily diffused well and uniformly into the semiconductor substrate.

[Organic Solvent (S)]

The diffusion agent composition usually contains an organic solvent (S) as a solvent so that a thin coating film can be formed. The type of the organic solvent (S) is not particularly limited as long as the object of the present invention is not impeded.

Furthermore, when the diffusion agent composition contains the hydrolyzable silane compound (B), the diffusion agent composition is preferably substantially free from water. The expression "the diffusion agent composition is preferably substantially free from water" means that the diffusion agent composition does not contain water in such an amount that the hydrolysis proceeds to a level that desired effect by the addition thereof cannot be obtained.

Specific examples of organic solvents (S) include: monoethers of glycols such as ethylene glycol monomethyl ether, ethylene glycol monoethyl ether, ethylene glycol monopropyl ether, ethylene glycol monobutyl ether, propylene glycol monomethyl ether, propylene glycol monoethyl ether, propylene glycol monopropyl ether, propylene glycol monobutyl ether, diethylene glycol monomethyl ether, diethylene glycol monoethyl ether, diethylene glycol monopropyl ether, diethylene glycol monobutyl ether, diethylene glycol monophenyl ether, dipropylene glycol monomethyl ether, dipropylene glycol monoethyl ether, dipropylene glycol monopropyl ether, dipropylene glycol monobutyl ether, dipropylene glycol monophenyl ether, triethylene glycol monomethyl ether, triethylene glycol monoethyl ether, tripropylene glycol monomethyl ether, and tripropylene glycol monoethyl ether; monoethers such as diisopentyl ether, diisobutyl ether, benzyl methyl ether, benzyl ethyl ether, dioxane, tetrahydrofuran, anisole, perfluoro-2-butyltetrahydrofuran, and perfluorotetrahydrofuran; chain diethers of glycols such as ethylene glycol dimethyl ether, ethylene glycol diethyl ether, ethylene ethylene glycol dipropyl ether, ethylene glycol dibutyl ether, propylene glycol dimethyl ether, propylene glycol diethyl ether, propylene glycol dipropyl ether, propylene glycol dibutyl ether, diethylene glycol dimethyl ether, diethylene glycol diethyl ether, diethylene glycol dipropyl ether, diethylene glycol dibutyl ether, dipropylene glycol dimethyl ether, dipropylene glycol diethyl ether, dipropylene glycol dipropyl ether, and dipropylene glycol dibutyl ether; cyclodiethers such as 1,4-dioxane; ketones such as 1-octanone, 2-octanone, 1-nonanone, 2-nonanone, acetone, 2-heptanone, 4-heptanone, 1-hexanone, 2-hexanone, 3-pentanone, diisobutyl ketone, cyclohexanone, methylcyclohexanone, phenylacetone, methylethyl ketone, methylisobutyl ketone, ethylisobutyl ketone, acetylacetone, acetonylacetone, ionone, diacetonyl alcohol, acetyl carbinol, acetophenone, methyl naphthyl ketone, and isophorone; esters such as methyl acetate, butyl acetate, ethyl acetate, isopropyl acetate, pentyl acetate, isopentyl acetate, methoxy ethyl acetate, ethoxy ethyl acetate, ethylene glycol monomethyl ether acetate, ethylene glycol monoethyl ether acetate, ethylene glycol monopropyl ether acetate, ethylene glycol monobutyl ether acetate, ethylene glycol monophenyl ether acetate, propylene glycol monomethyl ether acetate, propylene glycol monoethyl ether acetate, propylene glycol monopropyl ether acetate, propylene glycol monobutyl ether acetate, propylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl carbonate, propyl carbonate, butyl carbonate, methylpyrubate, ethylpyrubate, propylpyrubate, butyl pyrubate, methyl acetoacetate, ethyl acetoacetate, methyl propionate, ethyl propionate, propyl propionate, isopropyl propionate, methyl-3-methoxypropionate, ethyl-3-methoxypropionate, ethyl-3-ethoxypropionate, propyl-3-methoxy propionate, and isopropyl-3-methoxypropionate, propylene carbonate, and γ-butyrolactone; amide-based solvents containing no active hydrogen atom, such as N-methyl-2-pyrrolidone, N,N-dimethylacetamide, N,N-dimethylformamide, hexamethylphosphoric triamide, and 1,3-dimethyl-2-imidazolidinone; sulfoxides such as dimethyl sulfoxide; aliphatic hydrocarbon-based solvents optionally containing a halogen atom such as pentane, hexane, octane, decane, 2,2,4-trimethylpentane, 2,2,3-trimethylhexane, perfluorohexane, perfluoroheptane, limonene, and pinene; aromatic hydrocarbon-based solvents such as benzene, toluene, xylene, ethylbenzene, propylbenzene, 1-methylpropylbenzene, 2-methylpropylbenzene, diethylbenzene, ethylmethylbenzene, trimethylbenzene, ethyldimethylbenzene, and dipropylbenzene; monovalent alcohols such as methanol, ethanol, n-propanol, isopropanol, butanol, isobutanol, 2-methoxyethanol, 2-ethoxyethanol, 3-methyl-3-methoxybutanol, hexanol, cyclohexanol, benzyl alcohol, and 2-phenoxyethanol; and glycols such as ethylene glycol, propylene glycol, diethylene glycol, and dipropylene glycol. In the above examples of preferred organic solvent (S), organic solvents containing an ether bond and an ester bond are classified in esters. They may be used alone or in a combination of two or more of these.

When the diffusion agent composition contains a hydrolyzable silane compound (B), the organic solvent (S) which does not have a functional group reactive with the hydrolyzable silane compound (B) is preferably used. In particular, when the hydrolyzable silane compound (B) contains an isocyanate group, the organic solvent (S) which does not have a functional group reactive with the hydrolyzable silane compound (B) is preferably used.

Functional groups reactive with the hydrolyzable silane compound (B) include both functional groups reactive directly with groups that are hydrolyzable to produce a hydroxyl group, and functional groups reactive with a hydroxyl group (a silanol group) produced by hydrolysis.

Examples of functional groups reactive with the hydrolyzable silane compound (B) include a hydroxyl group, a carboxyl group, an amino group, and halogen atoms.

Examples of suitable organic solvents that do not have a functional group reactive with the hydrolyzable silane compound (B) include, among the specific examples of the organic solvent (S), monoethers, chain diethers, cyclodiethers, ketones, esters, amide-based solvents that do not have an active hydrogen atom, sulfoxides, and aliphatic hydrocarbon-based solvents that may contain a halogen, and organic solvent recited as specific examples of the aromatic hydrocarbon-based solvents.

[Other Component]

The diffusion agent composition may contain various additives such as surfactants, antifoaming agents, pH adjustors, and viscosity modifiers as long as the object of the present invention is not impaired. Further, the diffusion agent composition may contain binder resins with a view to improving the coating property and film forming property. Various resins may be used as the binder resin, and acrylic resins are preferred.

The diffusion agent composition is obtained by homogeneously mixing the above components in respective predetermined amounts.

<<Method for Manufacturing Semiconductor Substrate>>

The method for manufacturing a semiconductor substrate includes:

applying the above-mentioned diffusion agent composition to form a coating film; and diffusing an impurity diffusion component (A) in the diffusion agent composition into a semiconductor substrate. Hereinafter, the step of forming a coating film is referred to also as a "coating step," and the step of diffusing the impurity diffusion component (A) into the semiconductor substrate is referred to also as a "diffusion step". The coating step and the diffusion step will be described in that order.

[Coating Step]

In the coating step, a diffusion agent composition is coated on a semiconductor substrate to form a coating film. Regarding the coating step, the diffusion agent composition, the semiconductor substrate and the coating method will be described in that order.

Semiconductor Substrate

Various substrates that have hitherto been used as a target of diffusion of an impurity diffusion component may be used as the semiconductor substrate without limitation. Silicon substrates are typically used as the semiconductor substrate. Since the impurity diffusion component contained in the diffusion agent composition contains boron, an n-type silicon substrate is suitable as the silicon substrate. The semiconductor substrate such as silicon substrate often has a natural oxide film formed by natural oxidation of the surface of the semiconductor substrate on the surface thereof. For example, the silicon substrate often has the natural oxide film mainly consisting of $SiO_2$. When the impurity diffusion component is diffused into the semiconductor substrate, the natural oxide film on the surface of the semiconductor substrate is typically removed by using an aqueous solution of hydrofluoric acid or the like. However, in case of using the above-mentioned diffusion agent composition, the natural oxide film on the surface of the semiconductor substrate may be removed or may not be removed. When the natural oxide film is not removed, the impurity diffusion component is a little more easily diffused well into the semiconductor substrate than when the natural oxide film is removed. For example, when the natural oxide film is not removed, it is considered that boron atoms (boron compounds) are effectively incorporated into a surface layer of the semiconductor substrate by incorporation of boron atoms (boron compounds) into the natural oxide film with relatively low silicon atom density. As a result, it is presumed that boron atoms are well diffused into the semiconductor substrate by forming a thin film like a borosilicate glass on the semiconductor substrate.

The semiconductor substrate may have a three-dimensional structure on its surface onto which the diffusion agent composition is to be applied. According to the present invention, even when the semiconductor substrate has on its surface the three-dimensional structure, particularly a three-dimensional structure having a nanoscale fine pattern, the impurity diffusion component can be diffused well and uniformly into the semiconductor substrate by coating the diffusion agent composition to form a thin coating film having a thickness of not more than, for example, 30 nm on the semiconductor substrate.

The shape of the pattern is not particularly limited, however typical examples thereof include linear or curved lines or grooves of a rectangular cross section and hole shapes.

When the semiconductor substrate has on its surface a repeating pattern of a plurality of parallel lines, as the three-dimensional structure, an interval between the lines may be not more than 1 μm, not more than 100 nm, not more than 60 nm, or not more than 20 nm. The height of the lines may be not less than 30 nm, not less than 100 nm, not less than 1 μm, or not less than 5 μm.

Application Method

The thickness of the coating film formed using the diffusion agent composition is not particularly limited. The diffusion agent composition is applied onto the semiconductor substrate so that the thickness of the coating film formed using the diffusion agent composition is not more than 30 nm, preferably 0.2 to 10 nm. The method for applying the diffusion agent composition is not particularly limited as long as a coating film having a desired thickness can be formed. Preferred applying methods for the diffusion agent composition include a spin coating method, an ink jet method, and spray coating method. Note here that the thickness of the coating film is an average of thickness values measured at five or more points with an ellipsometer.

The film thickness of the coating film is properly set to any desired thickness depending upon the shape of the semiconductor substrate and an arbitrarily determined degree of diffusion of the impurity diffusion component (A).

After the application of the diffusion agent composition onto the surface of the semiconductor substrate, the surface of the semiconductor substrate is preferably rinsed with an organic solvent. The thickness of the coating film can be made further uniform by rinsing the surface of the semiconductor substrate after the formation of the coating film. In particular, when the semiconductor substrate has on its surface a three-dimensional structure, the thickness of the coating film is likely to be thick at the bottom (stepped portion) of the three-dimensional structure. However, the thickness of the coating film can be made uniform by rinsing the surface of the semiconductor substrate after the formation of the coating film.

As the organic solvent for rinsing, the above-mentioned organic solvents that may be contained in the diffusion agent composition can be used.

[Diffusion Step]

In the diffusion step, the impurity diffusion component (A) contained in the thin coating film formed on the semiconductor substrate using the diffusion agent composition is diffused into the semiconductor substrate. Any method may be used without particular limitation for the diffusion of the impurity diffusion component (A) into the semiconductor substrate as long as the impurity diffusion component (A) can be diffused from the coating film formed of the diffusion agent composition by heating.

A typical method is heating a semiconductor substrate provided with a coating film of a diffusion agent composition formed thereon in a heating furnace such as an electric furnace. Conditions for heating are not particularly limited as long as the impurity diffusion component (A) is diffused to a desired extent.

In general, after the removal of organic substances in the coating film by firing under an atmosphere of an oxidizing gas, the semiconductor substrate is heated under an atmosphere of an inert gas to diffuse the impurity diffusion component (A) into the semiconductor substrate. Heating in firing of the organic substances is preferably carried out at a temperature of preferably 300 to 1000° C., more preferably 400 to 800° C., and preferably for 1 to 120 min, more preferably for 5 to 60 min. Heating in the diffusion of the impurity diffusion component (A) is preferably carried out at a temperature of not lower than 700° C. and not higher than 1400° C., and more preferably at not lower than 700° C. and lower than 1200° C., and preferably for 1 to 120 min, more preferably for 5 to 60 min. Since the diffusion agent composition including the above-mentioned impurity diffusion component (A) is used, even when, for example, a temperature at the time of diffusion is low such as not higher than 1000° C., the impurity diffusion component (A) is well diffused into the semiconductor substrate. Note here that since a typical composition of the present invention does not contain so many organic substances, heating for firing may be skipped.

When the temperature of the semiconductor substrate can be rapidly raised at not less than 25° C./sec to a predetermined diffusion temperature, the holding time of the diffusion temperature may be not more than 30 sec, not more than 10 sec, or even a very short time of less than 1 sec. In this case, the impurity diffusion component (A) can easily be diffused at a high concentration in a shallow region in the surface of the semiconductor substrate.

According to the method described above, even when a semiconductor substrate having on its surface a three-dimensional structure with nanometer-scale fine voids is used, the impurity diffusion component can be diffused well and uniformly into the semiconductor substrate while suppressing the occurrence of defects on the semiconductor substrate. Accordingly, the method according to the present invention is suitable for use in the manufacture of multigate elements having a three-dimensional microstructure. The method according to the present invention can suppress the occurrence of defects in the semiconductor substrate during the diffusion of the impurity diffusion component and thus is particularly suitable for use in the manufacture of CMOS elements such as CMOS image sensors, and semiconductor elements such as logic LSI devices.

EXAMPLES

The following Examples further illustrate the present invention but should not be construed as limiting the present invention.

Example 1 and Comparative Example 1

In Example 1, the following compound A1 was used as an impurity diffusion component (component (A)). In Comparative Example 1, the following compound A2 (triethylamine borane) was used as the component (A). In Comparative Example 2, the following compound A3 (pinacolborane) was used as the component (A). In Comparative Example 3, the following compound A4 (trimethylborate) was used as the component (A).

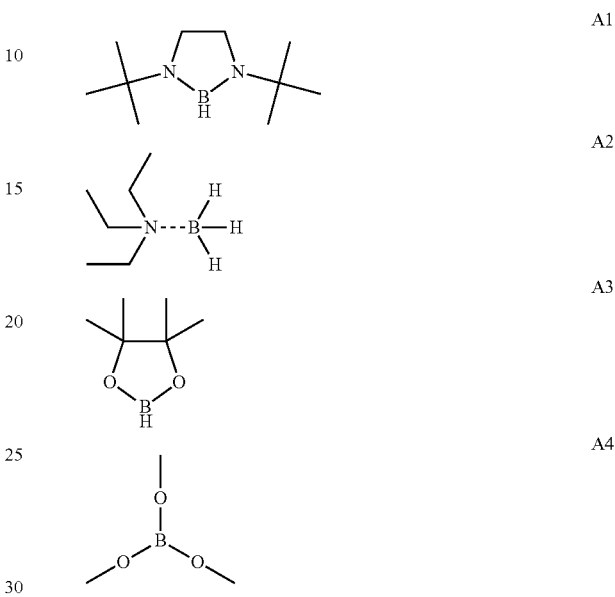

The above-mentioned components (A) were each dissolved in butyl acetate so that the concentration became 0.5 mass % to obtain diffusion agent compositions of Example 1 and Comparative Examples 1 to 3, respectively.

The diffusion agent compositions of the Example 1 and Comparative Examples 1 to 3 were respectively applied onto a surface of a silicon substrate having a flat surface (6 inches, n-type) using a spin coater to form coating films having thicknesses specified in Table 1. A substrate in which a natural oxide film on the surface was removed by immersing into an aqueous solution of hydrofluoric acid of concentration of 0.5% by mass was used as the silicon substrate. After the formation of the coating film, the impurity diffusion component was subjected to diffusion treatment according to the following method. Subsequently, heating was carried out at a temperature rise rate of 25° C./sec under a nitrogen atmosphere with a flow rate of 1 L/m using a rapid thermal annealing apparatus (a lamp annealing apparatus), and diffusion treatment was carried out at diffusion temperatures specified in Table 1 and for a diffusion time of one second. The starting point of the diffusion time is a point of time at which the temperature of the substrate has reached the predetermined diffusion temperature. After the completion of the diffusion, the semiconductor substrate was rapidly cooled to room temperature.

As a result of the diffusion treatment of the impurity diffusion component, it was determined whether or not the type of the semiconductor substrate was reversed from n-type to p-type. Evaluation results are shown in Table 1, wherein a case where the type was reversed was evaluated as "Good", and a case where the type was not reversed was evaluated as "Bad". Note here that the diffusion test was carried out sequentially from a condition at a temperature of 1200° C., and the diffusion test was not carried out at lower temperatures from a temperature at which "Bad" evaluation was firstly given.

TABLE 1

| | Component (A) Type | Thickness of coating film (nm) | Diffusion temperature (° C.) | | | |
|---|---|---|---|---|---|---|
| | | | 1200 | 1100 | 1000 | 900 |
| Example 1 | A1 | 3.2 to 3.8 | Good | Good | Good | Good |
| Comparative Example 1 | A2 | 0.1 to 0.2 | Good | Bad | — | — |
| Comparative Example 2 | A3 | 0.1 | Good | Bad | — | — |
| Comparative Example 3 | A4 | 0.1 to 0.2 | Good | Bad | — | — |

According to Table 1, it is shown that in Example 1 using a component (A) having a structure that is easily adsorbed by a substrate surface and can be applied onto the surface of the semiconductor substrate to form a diffusion layer having a thickness of several nm, the component (A) was well diffused into the semiconductor substrate even at not higher than 1100° C. Note here that in Example 1, a sheet resistance value of the semiconductor substrate that had been subjected to diffusion treatment at 1200° C. was 593 (Ω/sq.); a sheet resistance value of the semiconductor substrate that had been subjected to diffusion treatment at 1100° C. was 682 (Ω/sq.); a sheet resistance value of the semiconductor substrate that had been subjected to diffusion treatment at 1000° C. was 1552 (Ω/sq.); and a sheet resistance value of the semiconductor substrate that had been subjected to diffusion treatment at 900° C. was 50447 (Ω/sq.).

On the other hand, from Comparative Example 1, in Comparative Examples 1 to 3 using a component (A) having a structure that is not easily adsorbed by the substrate surface in which a boron atom is tetravalent or a nitrogen atom is not contained, only a very thin film having a film thickness of not more than 0.2 nm can be obtained, and at a temperature of not higher than 1100° C., the component (A) was not well diffused into the surface of the semiconductor substrate.

Example 2

In Example 2, the following compound A5 was used as the impurity diffusion component (component (A)).

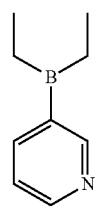

A5

The above-mentioned component (A) was dissolved in butyl acetate so that the concentration became 0.5 mass % to obtain a diffusion agent composition of Example 2.

The diffusion agent composition of the Example 2 was applied onto a surface of a silicon substrate having a flat surface (6 inches, n-type) using a spin coater. After application, the coating film was rinsed with n-butyl acetate, thus forming a coating film having a film thickness of 1.7 nm. A substrate in which a natural oxide film on the surface was removed by immersing into an aqueous solution of hydrofluoric acid of concentration of 0.5% by mass was used as the silicon substrate. After the formation of the coating film, diffusion treatment of the impurity diffusion component was carried out at diffusion temperatures of 1000° C. and 1100° C. in the same manner as in Example 1. As a result, a sheet resistance value of the semiconductor substrate that had been subjected to diffusion treatment at 1000° C. was 9699 (Ω/sq.), and a sheet resistance value of the semiconductor substrate that had been subjected to diffusion treatment at 1100° C. was 1748 (Ω/sq.). From these results, it is shown that when the diffusion agent composition of Example 2 is used, the component (A) is well diffused at diffusion temperatures of not higher than 1100° C.

Example 3

In Example 3, the following compound A6 was used as the impurity diffusion component (component (A)).

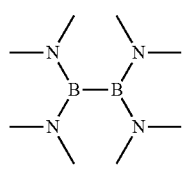

A6

The above-mentioned component (A) was dissolved in butyl acetate so that the concentration became 0.5 mass % to obtain a diffusion agent composition of Example 3.

The diffusion agent composition of the Example 3 was applied onto a surface of a silicon substrate having a flat surface (6 inches, n-type) using a spin coater to form a coating film having a film thickness of 27 nm. A substrate in which a natural oxide film on the surface was removed by immersing into an aqueous solution of hydrofluoric acid of concentration of 0.5% by mass was used as the silicon substrate. After the formation of the coating film, diffusion treatment of the impurity diffusion component was carried out at diffusion temperatures of 900° C., 1000° C., and 1100° C., respectively by the same manner as in Example 1. As a result, a sheet resistance value of the semiconductor substrate that had been subjected to diffusion treatment at 900° C. was 7338 (Ω/sq.), a sheet resistance value of the semiconductor substrate that had been subjected to diffusion treatment at 1000° C. was 1075 (Ω/sq.), and a sheet resistance value of the semiconductor substrate that had been subjected to diffusion treatment at 1100° C. was 596 (Ω/sq.). From these results, when the diffusion agent composition of Example 3 is used, it is shown that the components (A) are well diffused at diffusion temperatures of not higher than 1100° C.

Examples 4 to 11

In Examples 4 to 11, the following compounds A7 to A13 were used as the impurity diffusion component (component (A)).

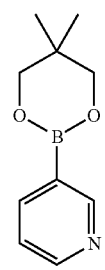

A7

-continued

A8
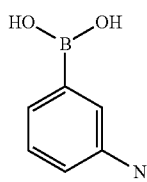

A9
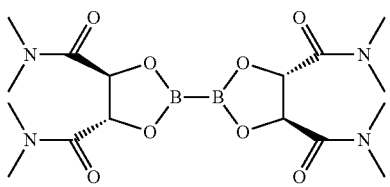

A10
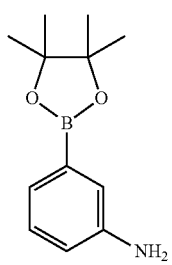

A11
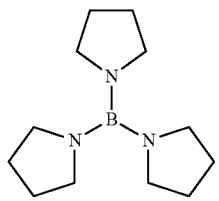

A12
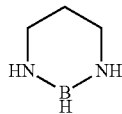

A13
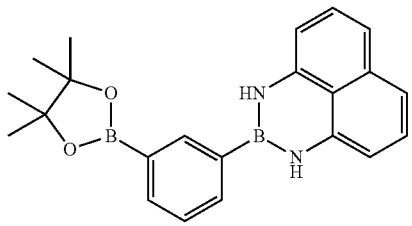

The components (A) of types described in Table 2 were dissolved in solvents of types described in Table 2, respectively, so that the concentration became 0.5 mass % to obtain diffusion agent compositions of Examples 4 to 11, respectively.

The diffusion agent compositions of the Examples 4 to 11 were applied onto a surface of a silicon substrate having a flat surface (6 inches, n-type) using a spin coater to form coating films described in Table 2, respectively. A substrate in which a natural oxide film on the surface was removed by immersing into an aqueous solution of hydrofluoric acid of concentration of 0.5% by mass was used as the silicon substrate. Note here that in Example 11, after the application, rinsing with butyl acetate was carried out. After the formation of the coating film, diffusion treatment of the impurity diffusion component was carried out at diffusion temperature of 1000° C. in the same manner as in Example 1. In any Examples, the semiconductor substrates after diffusion treatment were reversed from n-type to p-type. The sheet resistance values of the semiconductor substrates after diffusion treatment are shown in Table 2.

TABLE 2

| | Component (A) Type | Organic solvent (S) Type | Rinse | Thickness of coating film (nm) | Sheet resistance (Ω/sq.) |
|---|---|---|---|---|---|
| Example 4 | A7 | Isopropanol | Not rinsed | 51.5 | 2366 |
| Example 5 | A8 | Isopropanol | Not rinsed | 46.9 | 2273 |
| Example 6 | A9 | Isopropanol | Not rinsed | 53.8 | 12153 |
| Example 7 | A10 | Butyl acetate | Not rinsed | 31.4 | 85253 |
| Example 8 | A11 | Butyl acetate | Not rinsed | 10.4 | 172 |
| Example 9 | A7 | Isopropanol | Rinsed | 2.4 | 7419 |
| Example 10 | A12 | Butyl acetate | Rinsed | 23.9 | 254 |
| Example 11 | A13 | Butyl acetate | Not Rinsed | 32.4 | 9497 |

According to Table 2, it is shown that in Examples 4 to 11 using a component (A) having a structure that is easily adsorbed by a substrate surface and can be applied onto the surface of the semiconductor substrate to form a diffusion layer, the component (A) was well diffused into the semiconductor substrate at 1000° C.

Example 12

The above-mentioned compound A1 was used as the component (A). The component (A) was dissolved in butyl acetate so that the concentration became 1.0 mass % to obtain a diffusion agent composition. Subsequently, a diffusion agent composition was applied onto a surface of a silicon substrate (n-type) provided with a plurality of grooves each having a width of 500 nm and a depth of 2.8 μm using a spin coater to form a coating film. A substrate in which a natural oxide film on the surface was removed by immersing into an aqueous solution of hydrofluoric acid of concentration of 0.5% by mass was used as the silicon substrate. After the application, rinsing with butyl acetate was carried out. Such application operations were repeated 10 times to form a coating film having a film thickness of 17.4 nm. Note here that the application operations were repeated 10 times because a formation state of the coating film was easily observed.

When the cross-section of the semiconductor substrate after the formation of the coating film was observed under an electron microscope, it was shown that the coating film was formed substantially uniformly on the all surface of the inner surface of the recess portions (grooves).

Subsequently, heating was carried out at a temperature rise rate of 25° C./sec under a nitrogen atmosphere with a flow rate of 1 L/m using a rapid thermal annealing apparatus (a lamp annealing apparatus) and diffusion treatment was carried out at a diffusion temperature of 1100° C. and for a diffusion time for ten seconds. The starting point of the diffusion time is a point of time at which the temperature of the substrate has reached the predetermined diffusion temperature. After the completion of the diffusion, the semiconductor substrate was rapidly cooled to room temperature.

The surface of the semiconductor substrate after the diffusion treatment was observed by Scanning Capacitance Microscopy (SCM method), and carrier distribution on the surface of the semiconductor substrate was determined, the whole surface of the semiconductor substrate having concavity and convexity was substantially uniformly reversed to p-type.

Example 13

The above-mentioned compound A1 was used as the component (A). The component (A) was dissolved in butyl acetate so that the concentration became 1.0 mass % to obtain a diffusion agent composition. Subsequently, a diffusion agent composition was applied onto a surface of a SiN substrate provided with a plurality of grooves each having a width of 80 nm and a depth of 200 nm using a spin coater. After the application, rinsing was carried out with butyl acetate. When the cross-section of the semiconductor substrate after the formation of the coating film was observed under an electron microscope, it was shown that the coating film was formed substantially uniformly on the all surface of the inner surface of the recess portions (grooves).

Example 14 to 25

The above-mentioned compound A1 and a hydrolyzable silane compound (B) (component (B), an alkoxysilane compound) were dissolved in butyl acetate at concentrations described in Tables 3, respectively, so as to obtain diffusion agent compositions of Examples 14 to 25. The components (B) specified in Table 3 are as follows.
B1: methyltriethoxysilane
B2: dimethyldimethoxysilane
B3: phenyltriethoxysilane The diffusion agent compositions of the Examples 14 to 25 were applied onto a surface of a silicon substrate having a flat surface (6 inches, n-type) using a spin coater and rinsed with butyl acetate to form a coating film described in Table 3. A substrate in which a natural oxide film on the surface was removed by immersing into an aqueous solution of hydrofluoric acid of concentration of 0.5% by mass was used as the silicon substrate. After the formation of the coating film, diffusion treatment of the impurity diffusion component was carried out at diffusion temperature of 1000° C. in the same manner as in Example 1. In any Examples, the semiconductor substrates after diffusion treatment were reversed from n-type to p-type. The sheet resistance values of the semiconductor substrates after diffusion treatment are shown in Table 3.

TABLE 3

| | Compound A1 Concentration (% by mass) | Component (B) Type | Component (B) Concentration (% by mass) | Thickness of coating film (nm) | Sheet resistance (Ω/sq.) |
|---|---|---|---|---|---|
| Example 14 | 1 | B1 | 0.5 | 3.3 | 4490 |
| Example 15 | 1 | B1 | 1 | 4.1 | 1280 |
| Example 16 | 5 | B1 | 0.5 | 7.8 | 3287 |
| Example 17 | 5 | B1 | 1 | 9.9 | 176 |
| Example 18 | 5 | B1 | 30 | 22.0 | 49 |
| Example 19 | 10 | B1 | 1 | 15.0 | 173 |
| Example 20 | 5 | B2 | 0.5 | 4.5 | 1041 |
| Example 21 | 5 | B2 | 1 | 5.7 | 818 |
| Example 22 | 5 | B2 | 3 | 6.2 | 550 |
| Example 23 | 5 | B3 | 0.5 | 4.8 | 540 |
| Example 24 | 5 | B3 | 1 | 7.0 | 239 |
| Example 25 | 5 | B3 | 3 | 11.6 | 176 |

According to Examples 13 to 24, in a case of using a diffusion agent composition containing the component (A) having a structure that is easily adsorbed by a substrate surface and can be applied onto the surface of the semiconductor substrate to form a diffusion layer, it is shown that even when the diffusion agent composition includes a hydrolyzable silane compound (B), the component (A) can be well diffused into the semiconductor substrate at 1000° C.

Example 26 and Example 27

In Example 26 and Example 27, the above-mentioned compound A1 was used as the impurity diffusion component (component (A)). In Example 26 and Example 27, a liquid obtained by dissolving the component (A) in butyl acetate so that the concentration became 1.0 mass % was used as a diffusion agent composition.

The diffusion agent compositions were respectively applied onto a surface of silicon substrates each having a flat surface (6 inches, n-type) using a spin coater and rinsed with butyl acetate to form coating films each having a thickness of 3.0 nm. In Example 26, a silicon substrate having a natural oxide film on a surface thereof was used. In Example 27, a substrate in which a natural oxide film on the surface was removed by immersing into an aqueous solution of hydrofluoric acid of concentration of 0.5% by mass was used as the silicon substrate.

After the formation of the coating film, the impurity diffusion component was subjected to diffusion treatment according to the following method. Heating was carried out at a temperature rise rate of 15° C./sec under a nitrogen atmosphere with a flow rate of 1 L/m using a rapid thermal annealing apparatus (a lamp annealing apparatus), and diffusion treatment was carried out at diffusion temperature of 950° C. and for a diffusion time of 25 seconds. The starting point of the diffusion time is a point of time at which the temperature of the substrate has reached the predetermined diffusion temperature. After the completion of the diffusion, the semiconductor substrate was rapidly cooled to room temperature.

In both of Example 26 and Example 27, the semiconductor substrates after diffusion treatment were reversed from n-type to p-type. The sheet resistance values of the semiconductor substrates after diffusion treatment are shown in Table 4.

TABLE 4

| | Compound A1 Concentration (% by mass) | Removal of natural oxide film | Sheet resistance (Ω/sq.) |
|---|---|---|---|
| Example 26 | 1 | Done | 883.4 |
| Example 27 | 1 | Not Done | 1281.7 |

According to Example 26 and Example 27, it is shown that the impurity diffusion component is diffused well in case where the natural oxide film on the surface of silicon substrate was removed or not removed. Further, a comparison of Example 26 and Example 27 shows that, when the natural oxide film is not removed, the impurity diffusion component is more easily diffused well than when the natural oxide film is removed.

What is claimed is:

1. A diffusion agent composition used for diffusion of impurities into a semiconductor substrate, comprising an impurity diffusion component (A) which can be applied onto a surface of a semiconductor substrate to form a diffusion layer, and
an organic solvent (S),
wherein said impurity diffusion component (A) is a boron compound including a nitrogen atom, and
wherein the boron compound is a compound represented by the following formula (a1) or the following formula (a2):

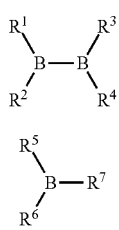

wherein $R^1$, $R^2$, $R^3$, and $R^4$ each independently represents a hydrogen atom, a hydroxyl group, an organic group which does not contain a nitrogen atom, or a nitrogen atom-containing group; at least one of $R^1$, $R^2$, $R^3$, and $R^4$ is a nitrogen atom-containing group; and $R^1$ and $R^2$, $R^2$ and $R^4$, $R^3$ and $R^4$, as well as $R^1$ and $R^3$, may each independently be bonded to each other to form a ring, and in the formula (a2), $R^5$, $R^6$, and $R^7$ each independently represents a hydrogen atom, a hydroxyl group, an organic group which does not contain a nitrogen atom, or a nitrogen atom-containing group; at least one of $R^5$, $R^6$, and $R^7$ is a nitrogen atom-containing group; and two of $R^5$, $R^6$, and $R^7$ may be bonded to each other to form a ring.

2. A method for manufacturing a semiconductor substrate, the method comprising:
applying the diffusion agent composition according to claim 1 onto a semiconductor substrate to form a coating film; and
diffusing the impurity diffusion component (A) in the diffusion agent composition into the semiconductor substrate,
wherein the coating film is heated at a temperature of 900° C. or more and 1200° C. or less to diffuse the impurity diffusion component (A) into the semiconductor substrate.

3. The method for manufacturing a semiconductor substrate according to claim 2, wherein the coating film has a film thickness of not more than 30 nm.

4. The method for manufacturing a semiconductor substrate according to claim 3, wherein the coating film has a thickness of 0.2 to 10 nm.

5. The method for manufacturing a semiconductor substrate according to claim 2, wherein the semiconductor substrate has a three-dimensional structure having convexes and concaves on a surface onto which the diffusion agent composition is applied.

6. The method for manufacturing a semiconductor substrate according to claim 2, further comprising rinsing the coating film with an organic solvent.

7. The diffusion agent composition according to claim 1, wherein the boron compound is a compound selected from the group consisting of compounds represented by the following formulae (a1-1), (a1-2), (a2-1), (a2-2), (a2-3), (a2-4), and (a2-5):

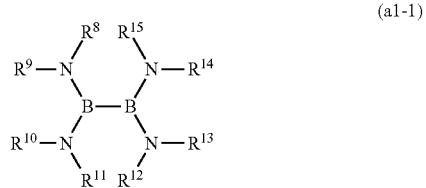

wherein in the formula (a1-1), $R^8$ to $R^{15}$ each independently represents a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms; $R^8$ and $R^9$, $R^{10}$ and $R^{11}$, $R^{12}$ and $R^{13}$, as well as $R^{14}$ and $R^{15}$, may each independently be bonded to each other to form a ring;

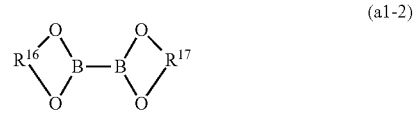

wherein in the formula (a1-2), $R^{16}$ and $R^{17}$ each represent a divalent organic group;

wherein in the formula (a2-1), $R^{29}$ represents a nitrogen-containing heterocyclic group or a cyclic group which does not contain a nitrogen atom substituted with a nitrogen-containing group; $R^{30}$ and $R^{31}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms; $R^{30}$ and $R^{31}$ may be bonded to each other to form a ring;

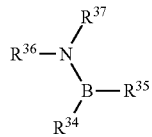

(a2-2)

wherein in the formula (a2-2), $R^{34}$ and $R^{35}$ each independently represent a hydrogen atom, a hydroxyl group, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms; and $R^{36}$ and $R^{37}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms; $R^{34}$ and $R^{35}$ may be bonded to each other to form a ring; $R^{34}$ and $R^{36}$ may be bonded to each other to form a ring; $R^{35}$ and $R^{37}$ may be bonded to each other to form a ring; and $R^{36}$ and $R^{37}$ may be bonded to each other to form a ring;

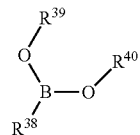

(a2-3)

wherein in the formula (a2-3), $R^{38}$ represents a nitrogen-containing heterocyclic group or a cyclic group which does not contain a nitrogen atom substituted with a nitrogen-containing group; $R^{39}$ and $R^{40}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms; $R^{39}$ and $R^{40}$ may be bonded to each other to form a ring;

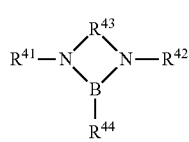

(a2-4)

wherein the formula (a2-4), $R^{41}$ and $R^{42}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms $R^{43}$ represents an alkylene group having 1 to 10 carbon atoms, —$BR^{45}$—, —$BR^{45}$—$BR^{45}$—, —$BR^{45}$—$NR^{46}$—, —$NR^{46}$—$NR^{46}$—, —$BR^{45}$—$NR^{46}$—$BR^{45}$—, or —$BR^{45}$—$NR^{46}$—$BR^{45}$—$NR^{46}$—$BR^{45}$—; $R^{46}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms; $R^{44}$ and $R^{45}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, and an aromatic acyl group having 7 to 11 carbon atoms, a nitrogen-containing heterocyclic group, or a cyclic group which does not contain a nitrogen atom substituted with a nitrogen-containing group; and

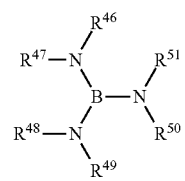

(a2-5)

wherein in the formula (a2-5), $R^{46}$ to $R^{51}$ each independently represent a hydrogen atom, an aliphatic hydrocarbon group having 1 to 10 carbon atoms, an aromatic hydrocarbon group having 6 to 10 carbon atoms, an aralkyl group having 7 to 12 carbon atoms, an aliphatic acyl group having 2 to 10 carbon atoms, or an aromatic acyl group having 7 to 11 carbon atoms; $R^{46}$ and $R^{47}$, $R^{48}$ and $R^{49}$, and $R^{50}$ and $R^{51}$ each independently may be bonded to each other to form a ring.

8. The diffusion agent composition according to claim 1, wherein the boron compound is a compound selected from the group consisting of compounds A1 and A5 to A13, represented by the following formulae:

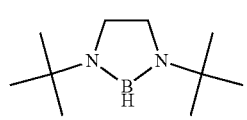

A1

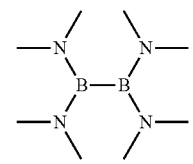

A5

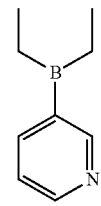

A6

-continued
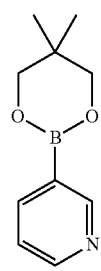
A7
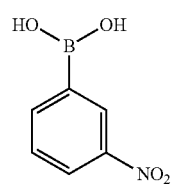
A8
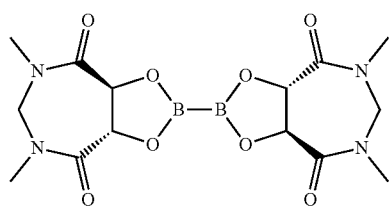
A9
-continued
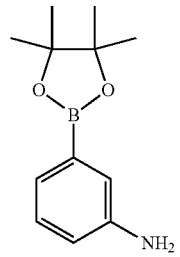
A10
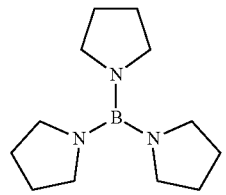
A11
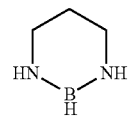
A12
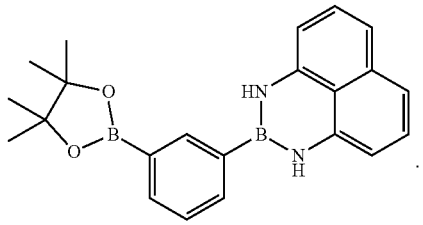
A13
* * * * *